United States Patent
Yeung et al.

(10) Patent No.: US 7,452,876 B2
(45) Date of Patent: *Nov. 18, 2008

(54) CYCLOPROPYL FUSED INDOLOBENZAZEPINE HCV NS5B INHIBITORS

(75) Inventors: Kap-Sun Yeung, Madison, CT (US); Katharine A. Grant-Young, Madison, CT (US); Min Ding, Glastonbury, CT (US); Robert G. Gentles, Wallingford, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/756,203

(22) Filed: May 31, 2007

(65) Prior Publication Data

US 2007/0287694 A1    Dec. 13, 2007

Related U.S. Application Data

(60) Provisional application No. 60/894,764, filed on Mar. 14, 2007, provisional application No. 60/804,203, filed on Jun. 8, 2006.

(51) Int. Cl.
*A61K 31/55* (2006.01)
*A61P 31/00* (2006.01)
*C07D 223/14* (2006.01)

(52) U.S. Cl. .................................. 514/214.01; 540/576

(58) Field of Classification Search ............ 514/214.01; 540/576

See application file for complete search history.

(56) References Cited

U.S. PATENT DOCUMENTS

| 7,153,848 B2 | 12/2006 | Hudyma et al. ........ 514/214.01 |
| 2006/0166964 A1 | 7/2006 | Hudyma et al. ........ 514/211.09 |
| 2007/0060565 A1 | 3/2007 | Meanwell et al. ...... 514/214.01 |
| 2007/0078122 A1 | 4/2007 | Bergstrom et al. ..... 514/214.01 |
| 2007/0185083 A1 | 8/2007 | Bergstrom et al. ..... 514/214.01 |

FOREIGN PATENT DOCUMENTS

| WO | WO2005/080399 | 9/2005 |
| WO | WO2006/040039 | 4/2006 |
| WO | WO2006/046030 | 5/2006 |
| WO | WO2007/029029 | 3/2007 |

OTHER PUBLICATIONS

U.S. Appl. No. 11/752,354, filed May 23, 2007, Robert G. Gentles et al.
U.S. Appl. No. 11/753,137, filed May 24, 2007, Carl P. Bergstrom.
U.S. Appl. No. 11/756,203, filed May 31, 2007, Kap-Sun Yeung et al.

*Primary Examiner*—Brenda L Coleman
(74) *Attorney, Agent, or Firm*—James Epperson

(57) ABSTRACT

The invention encompasses compounds as well as compositions and methods of using the compounds. The compounds have activity against hepatitis C virus (HCV) and are useful in treating those infected with HCV.

14 Claims, No Drawings

CYCLOPROPYL FUSED INDOLOBENZAZEPINE HCV NS5B INHIBITORS

CROSS-REFERENCE TO RELATED APPLICATIONS

This application claims the benefit of U.S. Provisional Application Ser. Nos. 60/894,764 filed Mar. 14, 2007 and 60/804,203 filed Jun. 8, 2006.

BACKGROUND OF THE INVENTION

Hepatitis C virus (HCV) is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma (Lauer, G. M.; Walker, B. D. N. *Engl. J. Med.* 2001, 345, 41-52).

HCV is a positive-stranded RNA virus. Based on a comparison of the deduced amino acid sequence and the extensive similarity in the 5'-untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome. At least six major genotypes have been characterized, and more than 50 subtypes have been described. The major genotypes of HCV differ in their distribution worldwide, and the clinical significance of the genetic heterogeneity of HCV remains elusive despite numerous studies of the possible effect of genotypes on pathogenesis and therapy.

The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protein with NS4A seems necessary to the processing events, enhancing the proteolytic efficiency at all of the sites. The NS3 protein also exhibits nucleoside triphosphatase and RNA helicase activities. NS5B (also referred to as HCV polymerase) is a RNA-dependent RNA polymerase that is involved in the replication of HCV. The HCV NS5B protein is described in "Structural Analysis of the Hepatitis C Virus RNA Polymerase in Complex with Ribonucleotides (Bressanelli; S. et al., *Journal of Virology* 2002, 3482-3492; and Defrancesco and Rice, *Clinics in Liver Disease* 2003, 7, 211-242.

Currently, the most effective HCV therapy employs a combination of alpha-interferon and ribavirin, leading to sustained efficacy in 40% of patients (Poynard, T. et al. *Lancet* 1998, 352, 1426-1432). Recent clinical results demonstrate that pegylated alpha-interferon is superior to unmodified alpha-interferon as monotherapy (Zeuzem, S. et al. *N. Engl J. Med.* 2000, 343, 1666-1672). However, even with experimental therapeutic regimens involving combinations of pegylated alpha-interferon and ribavirin, a substantial fraction of patients do not have a sustained reduction in viral load. Thus, there is a clear and important need to develop effective therapeutics for treatment of HCV infection.

DESCRIPTION OF THE INVENTION

One aspect of the invention is a compound of formula I

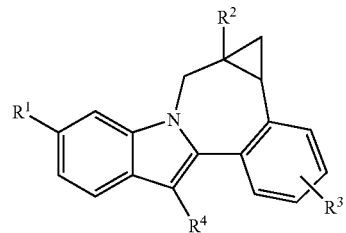

where:

$R^1$ is $CO_2R^5$ or $CONR^6R^7$;

$R^2$ is $N(R^{10})(R^{11})$;

$R^3$ is hydrogen, halo, alkyl, alkenyl, hydroxy, benzyloxy, alkoxy, or haloalkoxy;

$R^4$ is cycloalkyl;

$R^5$ is hydrogen or alkyl;

$R^6$ is hydrogen, alkyl, alkylSO$_2$, cycloalkylSO$_2$, haloalkylSO$_2$, $(R^7)(R^8)NSO_2$, or $(R^9)SO_2$;

$R^7$ is hydrogen or alkyl;

$R^8$ is hydrogen or alkyl;

$R^9$ is azetidinyl, pyrrolidinyl, piperidinyl, piperazinyl, morpholinyl, thiomorpholinyl, homopiperidinyl, or homomorpholinyl, and is substituted with 0-3 substituents selected from alkyl and alkoxy;

$R^{10}$ is hydrogen, alkyl, alkoxyCO, or $(R^{12})(R^{13})NCO$;

$R^{11}$ is hydrogen or alkyl;

$R^{12}$ is hydrogen, alkyl, alkoxyalkyl, aminoalkyl, (alkylamino)alkyl, (dialkylamino)alkyl, $(CO_2R^{14})$alkyl, $(CON(R^{15})(R^{16}))$alkyl, or (tetrahydropyranyl)alkyl;

$R^{13}$ is hydrogen alkyl, alkoxyalkyl, aminoalkyl, (alkylamino)alkyl, or (dialkylamino)alkyl;

or $(R^{12})(R^{13})N$ taken together is azetidinyl, pyrrolidinyl, piperidinyl, piperazinyl, morpholinyl, thiomorpholinyl, homopiperidinyl, or homomorpholinyl and is substituted with 0-3 substituents selected from alkyl and alkoxy;

$R^{14}$ is hydrogen or alkyl $R^{15}$ is hydrogen or alkyl; and $R^{16}$ is hydrogen or alkyl; or $N(R^{15})(R^{16})$ taken together is azetidinyl, pyrrolidinyl, piperidinyl, piperazinyl, morpholinyl, thiomorpholinyl, homopiperidinyl, or homomorpholinyl and is substituted with 0-3 substituents selected from alkyl and alkoxy;

or a pharmaceutically acceptable salt thereof.

Another aspect of the invention is a compound of formula I where $R^1$ is $CONHR^6$ and $R^6$ is $alkylSO_2$, $cycloalkylSO_2$, $haloalkylSO_2$, $(R^7)(R^8)NSO_2$, or $(R^9)SO_2$.

Another aspect of the invention is a compound of formula I where $R^3$ is hydrogen.

Another aspect of the invention is a compound of formula I where $R^3$ is methoxy.

Another aspect of the invention is a compound of formula I where $R^4$ is cyclohexyl.

Another aspect of the invention is a compound of formula I where $R^6$ is $(R^9)_2NSO_2$ or $(R^{10})SO_2$.

Another aspect of the invention is a compound of formula I where $R^{10}$ is $(R^{12})(R^{13})NCO$.

Another aspect of the invention is a compound of formula I where $R^{12}$ is alkoxyalkyl, (dialkylamino)alkyl, $(CON(R^{15})(R^{16}))$alkyl, or (tetrahydropyranyl)alkyl.

Another aspect of the invention is a compound of formula I where $(R^{12})(R^{13})N$ taken together is azetidinyl, pyrrolidinyl, piperidinyl, piperazinyl, morpholinyl, thiomorpholinyl, homopiperidinyl, or homomorpholinyl and is substituted with 0-3 substituents selected from alkyl and alkoxy.

Another aspect of the invention is a compound of formula I with the following stereochemistry.

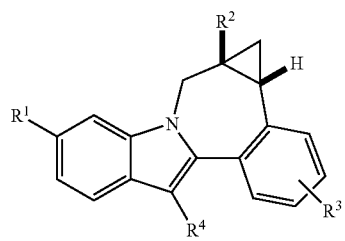

Another aspect of the invention is a compound of formula I with the following stereochemistry.

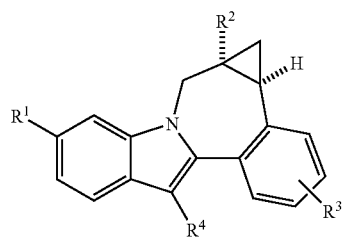

Any scope of any variable, including $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$, can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods known in the art.

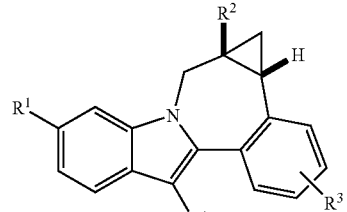

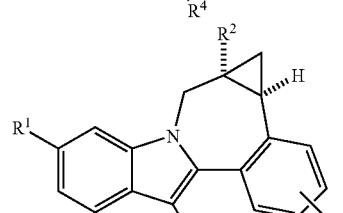

Synthetic Methods

The compounds may be made by methods known in the art including those described below. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification.

Abbreviations used in the schemes generally follow conventions used in the art.

The compounds can be made by methods known in the art and described in the application.

2-bromo-3-cyclohexyl-1H-indole-6-carboxylic acid can be condensed with a variety of sulfonyl ureas, using for example 1, 1'-carbonyldiimidazole in combination with 1,8-diazabicyclo[5.4.0]undec-7-ene in anhydrous THF. The resultant acyl sulfamides can be subjected to known coupling reactions, for example Suzuki coupling conditions with a diversity of 2-formyl boronic acids or esters to provide cyclic hemiaminal intermediates of the type depicted. These compounds can be converted to indolobenzazepines derivatives, using as one example, the methodology shown in Scheme 1. Related fused cyclopropyl ester derivatives can be generated by methods known in the art, including treatment of the indolobenzazepine esters with trimethyl sulfoxonium iodide under strongly basic conditions in DMSO. The residual aliphatic ester moiety in the resultant fused cyclopropanes can be hydrolyzed using sodium hydroxide in an aqueous methanolic THF mixture.

Scheme 1.

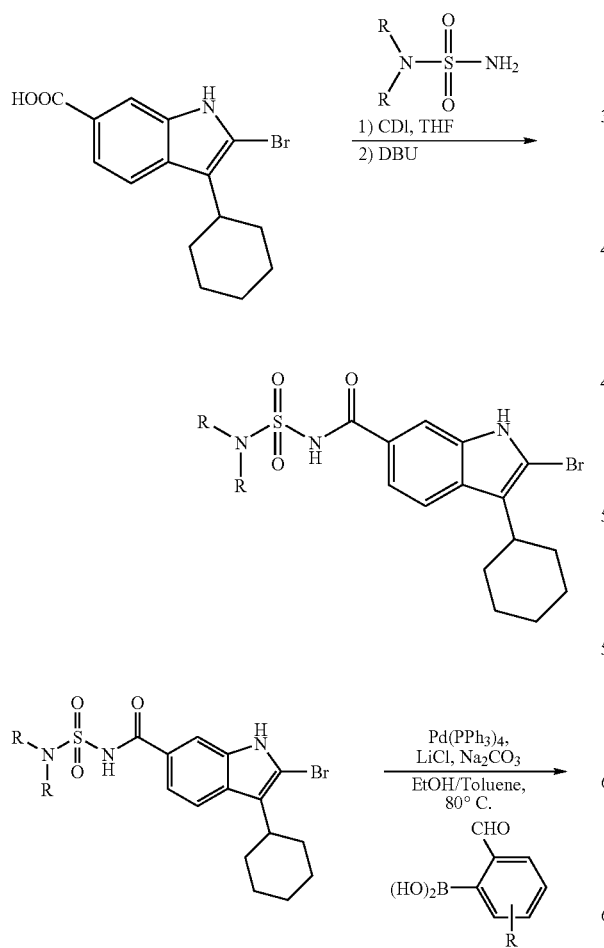

-continued

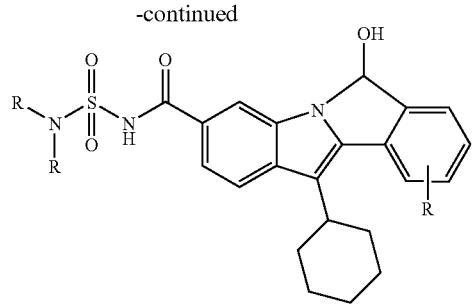

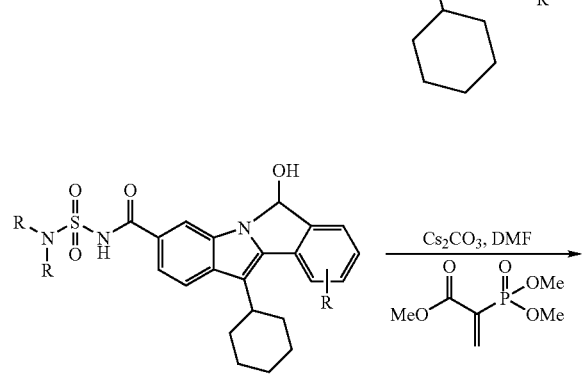

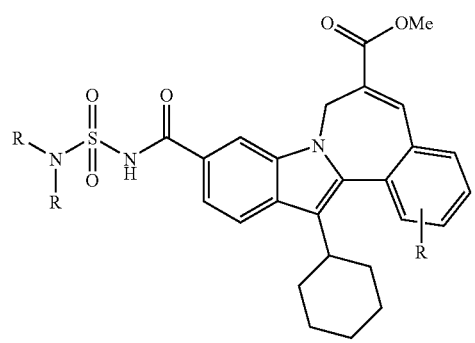

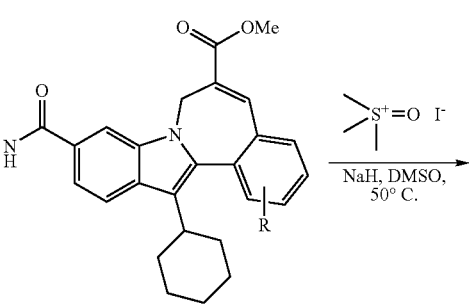

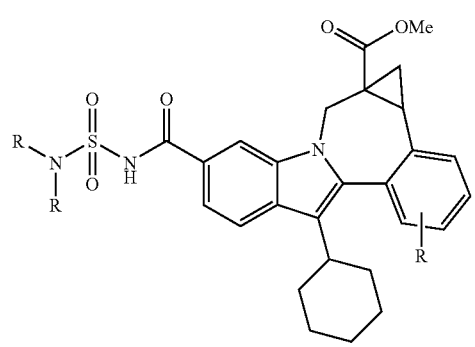

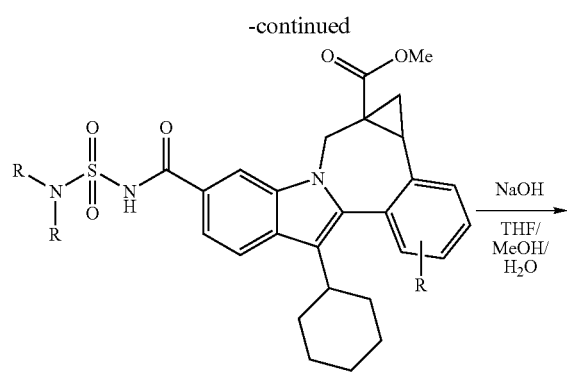
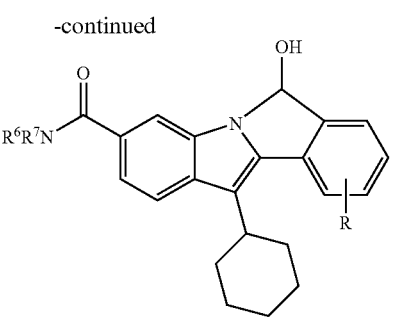
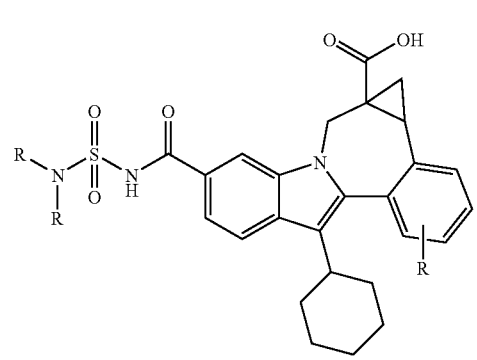
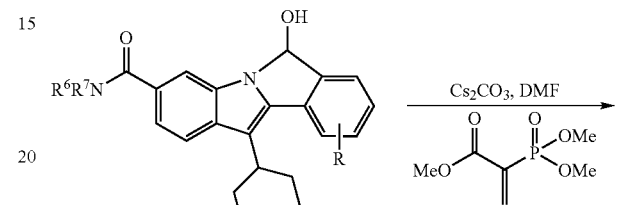
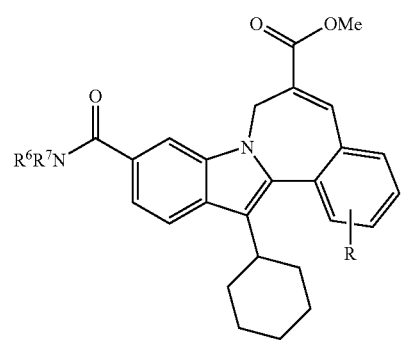
Scheme 1a.
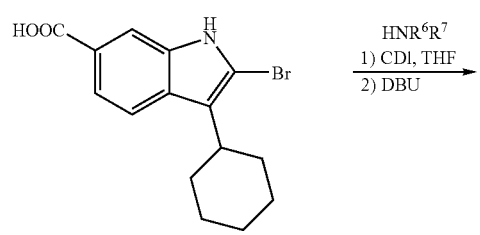
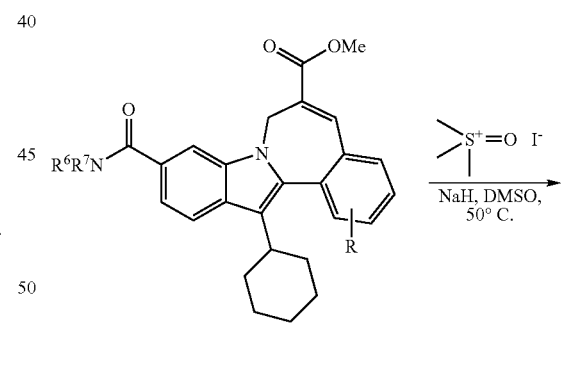
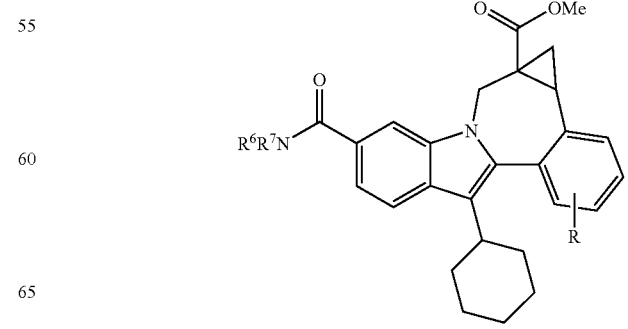

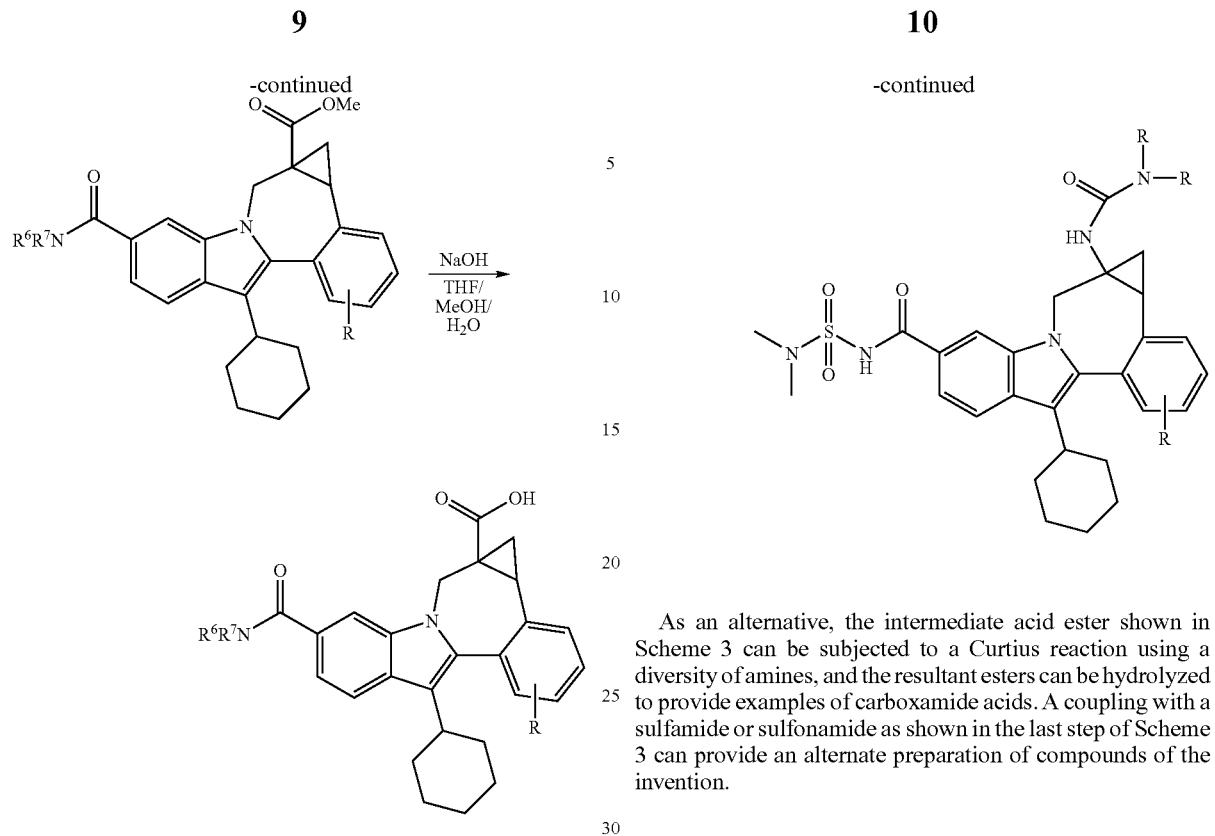

The resultant acids can be converted to ureas by methods known in the art, for example treatment with diphenylphosphoryl azide and triethylamine in toluene, and the intermediate acyl azide can be isolated, and then treated in a separate step with a diversity of amines to afford the urea examples as shown in Scheme 2.

As an alternative, the intermediate acid ester shown in Scheme 3 can be subjected to a Curtius reaction using a diversity of amines, and the resultant esters can be hydrolyzed to provide examples of carboxamide acids. A coupling with a sulfamide or sulfonamide as shown in the last step of Scheme 3 can provide an alternate preparation of compounds of the invention.

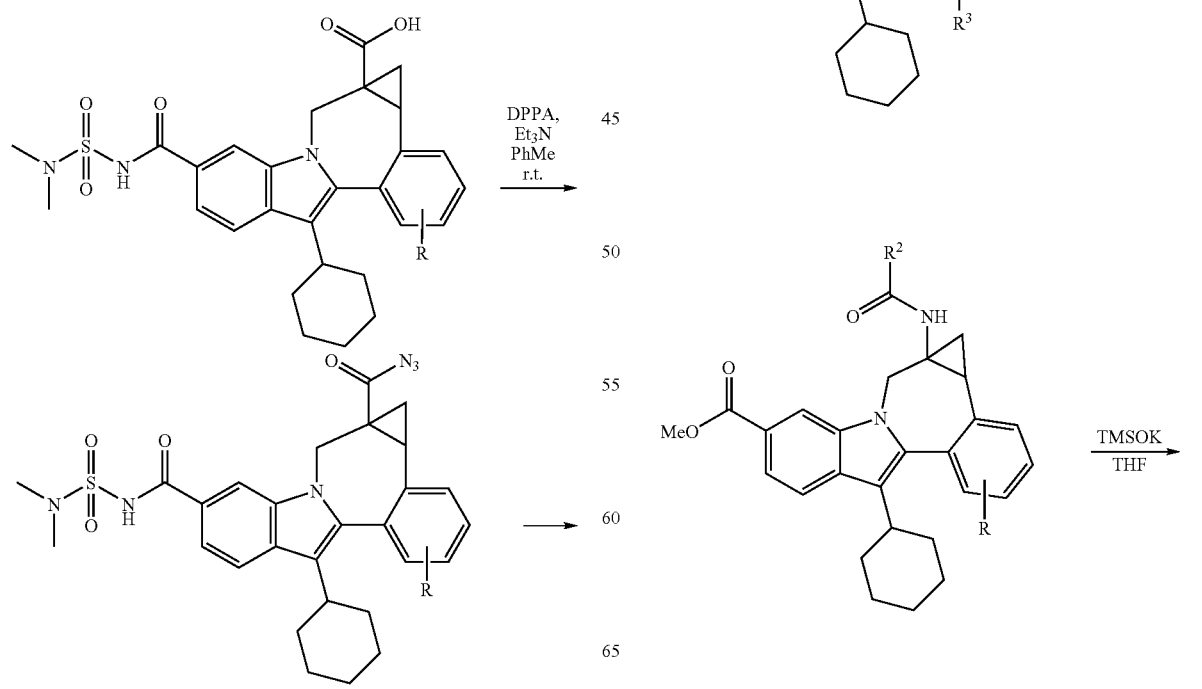

-continued

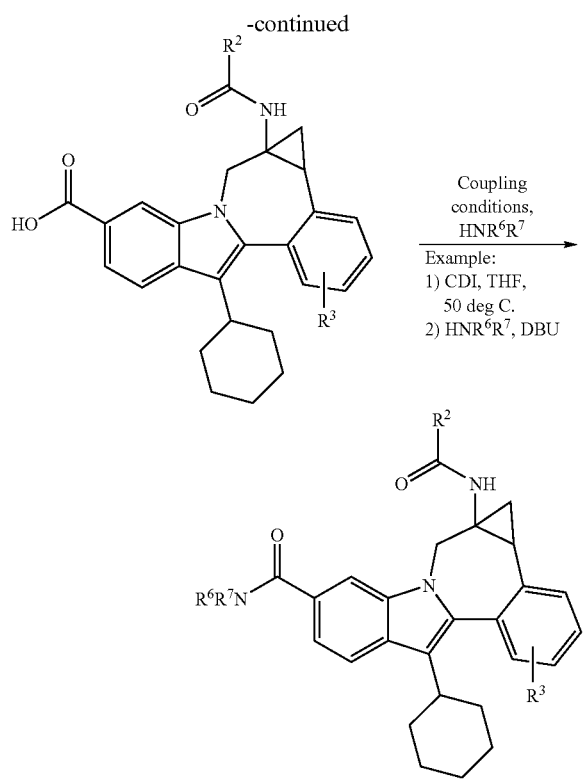

Biological Methods

The compounds demonstrated activity against HCV NS5B as determined in the following HCV RdRp assays.

HCV NS5B RdRp cloning, expression, and purification. The cDNA encoding the NS5B protein of HCV, genotype 1b, was cloned into the pET21a expression vector. The protein was expressed with an 18 amino acid C-terminal truncation to enhance the solubility. The *E. coli* competent cell line BL21 (DE3) was used for expression of the protein. Cultures were grown at 37° C. for ~4 hours until the cultures reached an optical density of 2.0 at 600 nm. The cultures were cooled to 20° C. and induced with 1 mM IPTG. Fresh ampicillin was added to a final concentration of 50 µg/ml and the cells were grown overnight at 20° C.

Cell pellets (3L) were lysed for purification to yield 15-24 mgs of purified NS5B. The lysis buffer consisted of 20 mM Tris-HCl, pH 7.4, 500 mM NaCl, 0.5% triton X-100, 1 mM DTT, 1 mM EDTA, 20% glycerol, 0.5 mg/ml lysozyme, 10 mM MgCl2, 15 ug/ml deoxyribonuclease I, and Complete TM protease inhibitor tablets (Roche). After addition of the lysis buffer, frozen cell pellets were resuspended using a tissue homogenizer. To reduce the viscosity of the sample, aliquots of the lysate were sonicated on ice using a microtip attached to a Branson sonicator. The sonicated lysate was centrifuged at 100,000×g for 1 hr at 4° C. and filtered through a 0.2 µm filter unit (Corning).

The protein was purified using three sequential chromatography steps: Heparin sepharose CL-6B, polyU sepharose 4B, and Hitrap SP sepharose (Pharmacia). The chromatography buffers were identical to the lysis buffer but contained no lysozyme, deoxyribonuclease I, MgCl2 or protease inhibitor and the NaCl concentration of the buffer was adjusted according to the requirements for charging the protein onto the column. Each column was eluted with a NaCl gradient which varied in length from 5-50 column volumes depending on the column type. After the final chromatography step, the resulting purity of the enzyme is >90% based on SDS-PAGE analysis. The enzyme was aliquoted and stored at −80° C.

Standard HCVNS5B RdRp enzyme assay. HCV RdRp genotype 1b assays were run in a final volume of 60 µl in 96 well plates (Costar 3912). The assay buffer is composed of 20 mM Hepes, pH 7.5, 2.5 mM KCl, 2.5 mM MgCl2, 1 mM DTT, 1.6 U RNAse inhibitor (Promega N2515), 0.1 mg/ml BSA (Promega R3961), and 2% glycerol. All compounds were serially diluted (3-fold) in DMSO and diluted further in water such that the final concentration of DMSO in the assay was 2%. HCV RdRp genotype 1b enzyme was used at a final concentration of 28 nM. A polyA template was used at 6 nM, and a biotinylated oligo-dT 12 primer was used at 180 nM final concentration. Template was obtained commercially (Amersham 27-4110). Biotinylated primer was prepared by Sigma Genosys. 3H-UTP was used at 0.6 µCi (0.29 µM total UTP). Reactions were initiated by the addition of enzyme, incubated at 30° C. for 60 min, and stopped by adding 25 µl of 50 mM EDTA containing SPA beads (4 µg/µl, Amersham RPNQ 0007). Plates were read on a Packard Top Count NXT after >1 hr incubation at room temperature.

Modified HCVNS5B RdRp enzyme assay. A modified enzyme assay was performed essentially as described for the standard enzyme assay except for the following: The biotinylated oligo dT12 primer was precaptured on streptavidin-coated SPA beads by mixing primer and beads in assay buffer and incubating at room temperature for one hour. Unbound primer was removed after centrifugation. The primer-bound beads were resuspended in 20 mM Hepes buffer, pH 7.5 and used in the assay at final concentrations of 20 nM primer and 0.67 µg/µl beads. Order of addition in the assay: enzyme (14 nM) was added to diluted compound followed by the addition of a mixture of template (0.2 nM), 3H-UTP (0.6 µCi, 0.29 µM), and primer-bound beads, to initiate the reaction; concentrations given are final. Reactions were allowed to proceed for 4 hours at 30° C.

$IC_{50}$ values for compounds were determined using seven different [I]. $IC_{50}$ values were calculated from the inhibition using the formula $y=A+((B-A)/(1+((C/x)\hat{\ }D)))$.

FRET Assay Preparation. To perform the HCV FRET screening assay, 96-well cell culture plates were used. The FRET peptide (Anaspec, Inc.) (Taliani et al., *Anal. Biochem.* 1996, 240, 60-67) contains a fluorescence donor, EDANS, near one end of the peptide and an acceptor, DABCYL, near the other end. The fluorescence of the peptide is quenched by intermolecular resonance energy transfer (RET) between the donor and the acceptor, but as the NS3 protease cleaves the peptide the products are released from RET quenching and the fluorescence of the donor becomes apparent. The assay reagent was made as follows: 5× cell Luciferase cell culture lysis reagent from Promega (#E153A) diluted to 1× with $dH_2O$, NaCl added to 150 mM final, the FRET peptide diluted to 20 uM final from a 2 mM stock.

To prepare plates, HCV replicon cells, with or without a *Renilla luciferase* reporter gene, were trypsinized and placed into each well of a 96-well plate with titrated test compounds added in columns 3 through 12; columns 1 and 2 contained a control compound (HCV protease inhibitor), and the bottom row contained cells without compound. The plates were then placed in a $CO_2$ incubator at 37° C.

Assays. Subsequent to addition of the test compounds described above (FRET Assay Preparation), at various times the plate was removed and Alamar blue solution (Trek Diagnostics, #00-100) was added per well as a measure of cellular toxicity. After reading in a Cytoflour 4000 instrument (PE Biosystems), plates were rinsed with PBS and then used for FRET assay by the addition of 30 ul of the FRET peptide assay reagent described above (FRET Assay Preparation) per well. The plate was then placed into the Cytoflour 4000 instrument which had been set to 340 excite/490 emission, automatic mode for 20 cycles and the plate read in a kinetic mode. Typically, the signal to noise using an endpoint analysis after the reads was at least three-fold. Alternatively, after Alamar blue reading, plates were rinsed with PBS, 50 ul of DMEM (high glucose) without phenol red was added and plates were then used for luciferase assay using the Promega Dual-Glo Luciferase Assay System.

Compound analysis was determined by quantification of the relative HCV replicon inhibition and the relative cytotoxicity values. To calculate cytoxicity values, the average Alamar Blue fluorescence signals from the control wells were set as 100% non-toxic. The individual signals in each of the compound test wells were then divided by the average control signal and multiplied by 100% to determine percent cytotoxicity. To calculate the HCV replicon inhibition values, an average background value was obtained from the two wells containing the highest amount of HCV protease inhibitor at the end of the assay period. These numbers were similar to those obtained from naïve Huh-7 cells.

The background numbers were then subtracted from the average signal obtained from the control wells and this number was used as 100% activity. The individual signals in each of the compound test wells were then divided by the averaged control values after background subtraction and multiplied by 100% to determine percent activity. $EC_{50}$ values for a protease inhibitor titration were calculated as the concentration which caused a 50% reduction in FRET or luciferase activity. The two numbers generated for the compound plate, percent cytoxicity and percent activity were used to determine compounds of interest for further analysis.

Representative data for compounds are reported in Table 1.

TABLE 1

| Structure | $IC_{50}$ (uM) | $EC_{50}$ (uM) |
|---|---|---|
| [structure] | B | E |
| [structure] | B | E |

TABLE 1-continued

| Structure | IC$_{50}$ (uM) | EC$_{50}$ (uM) |
|---|---|---|
| | B | E |
| | B | H |
| | B | H |

TABLE 1-continued

| Structure | IC$_{50}$ (uM) | EC$_{50}$ (uM) |
|---|---|---|
| | B | B |
| | B | B |
| | B | B |

TABLE 1-continued

| Structure | IC$_{50}$ (uM) | EC$_{50}$ (uM) |
|---|---|---|
| | B | B |
| | B | B |
| (Chiral) | B | B |

TABLE 1-continued

| Structure | IC$_{50}$ (uM) | EC$_{50}$ (uM) |
| --- | --- | --- |
| Chiral | B | B |
| | B | B |
| | B | B |

TABLE 1-continued

| Structure | IC$_{50}$ (uM) | EC$_{50}$ (uM) |
|---|---|---|
| | B | B |
| | B | |
| | Chiral | |

TABLE 1-continued

| Structure | IC$_{50}$ (uM) | EC$_{50}$ (uM) |
|---|---|---|
| [structure] | | |
| [structure] | B | B |

A >1 µM;
B 0.02 µM-1 µM;
EC$_{50}$: C > 10 µM;
D 1 µM-10 µM;
E 1.0 µM-0.07 µM;
F < 0.02 µM;
G > 0.37 µM.
IC$_{50}$ values were determined using the preincubation protocol.
EC50 values were determined using the FRET assay.

Pharmaceutical Compositions and Methods of Treatment

The compounds demonstrate activity against HCV NS5B and can be useful in treating HCV and HCV infection. Therefore, another aspect of the invention is a composition comprising a compound, or a pharmaceutically acceptable salt or solvate thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of inhibiting the function of the HCV NS5B protein comprising contacting the HCV NS5B protein with a compound or a pharmaceutically acceptable salt thereof.

Another aspect of the invention is a method of treating an HCV infection in a patient comprising administering to the patient a therapeutically effective amount of a compound or a pharmaceutically acceptable solvate or salt thereof. In another embodiment the compound is effective to inhibit the function of the HCV replicon.

In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable solvate or salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is the method where the other compound having anti-HCV activity is effective to inhibit the function of target in the HCV life cycle other than the HCV NS5B protein.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | BioMedicines Inc., Emeryville, CA |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |

TABLE 2-continued

| Brand Name | Type of Inhibitor or Target | Source Company |
|---|---|---|
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | IMPDH inhibitor | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| T67 | β-tubulin inhibitor | Tularik Inc., South San Francisco, CA |
| VX-497 | IMPDH inhibitor | Vertex Pharmaceuticals Inc., Cambridge, MA |
| VX-950/LY-570310 | serine protease inhibitor | Vertex Pharmaceuticals Inc., Cambridge, MA/Eli Lilly and Co. Inc., Indianapolis, IN |
| Omniferon | natural IFN-α | Viragen Inc., Plantation, FL |
| XTL-002 | monoclonal antibody | XTL Biopharmaceuticals Ltd., Rehovot, Isreal |

DESCRIPTION OF SPECIFIC EMBODIMENTS

Analytical HPLC and LC/MS were performed by using Shimadzu-VP instrument with UV detection at 220 nM and Waters Micromass. Biotage Horizon was used for flash chromatography as indicated.

Intermediate 1

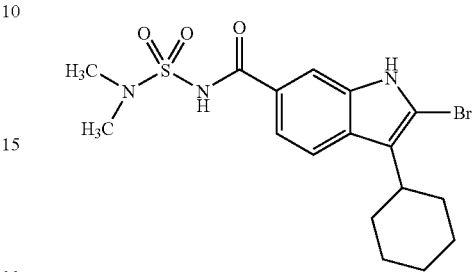

2-Bromo-3-cyclohexyl-N-[(dimethylamino)sulfonyl]-1H-indole-6-carboxamide. 1,1'-Carbonyldiimidazole (1.17 g, 7.2 mmol) was added to a stirred solution of 2-bromo-3-cyclohexyl-1H-indole-6-carboxylic acid (2.03 g, 6.3 mmol) in THF (6 mL) at 22° C. The evolution of $CO_2$ was instantaneous and when it slowed the solution was heated at 50° C. for 1 hr and then cooled to 22° C. N,N-Dimethylsulfamide (0.94 g, 7.56 mmol) was added followed by the dropwise addition of a solution of DBU (1.34 g, 8.8 mmol) in THF (4 mL). Stirring was continued for 24 hr. The mixture was partitioned between ethyl acetate and dilute HCl. The ethyl acetate layer washed with water followed by brine and dried over $Na_2SO_4$. The extract was concentrated to dryness to leave the title product as a pale yellow friable foam, (2.0 g, 74%, >90% purity, estimated from NMR). $^1$H NMR (300 MHz, DMSO-D6) δ ppm 1.28-1.49 (m, 3H) 1.59-2.04 (m, 7H) 2.74-2.82 (m, 1H) 2.88 (s, 6H) 7.57 (dd, J=8.42, 1.46 Hz, 1H) 7.74 (d, J=8.78 Hz, 1H) 7.91 (s, 1H) 11.71 (s, 1H) 12.08 (s, 1H).

Intermediate 2

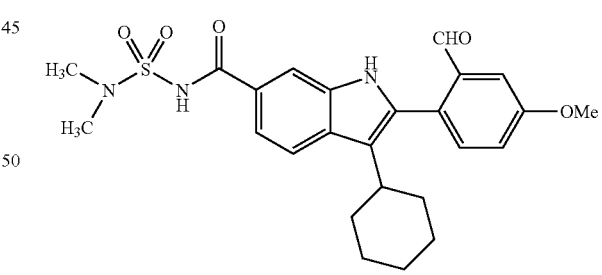

3-cyclohexyl-N-(N,N-dimethylsulfamoyl)-2-(2-formyl-4-methoxyphenyl)-1H-indole-6-carboxamide. A mixture of the 2-Bromo-3-cyclohexyl-N-[(dimethylamino)sulfonyl]-1H-indole-6-carboxamide (4.28 g, 0.01 mol), boronic acid (2.7 g, 0.015 mol), 2-dicyclohexylphosphino-2',6'-dimethoxy-biphenyl (41 mg, 0.0001 mol), palladium acetate (11.2 mg), and finely ground potassium carbonate (4.24 g, 0.02 mol) in toluene (30 mL) was stirred under reflux and under nitrogen for 30 min, at which time LC/MS analysis showed the reaction to be complete. The reaction mixture was then diluted with ethyl acetate and water, and then acidified with an excess of dilute HCl. The ethyl acetate layer was then collected and washed with dilute HCl, water and brine. The organic solution was then dried (magnesium sulfate), filtered and concentrated to give a gum. The gum was diluted with hexanes (250 ml) and ethyl acetate (25 mL), and the mixture was stirred for 20 hr at 22° C. during which time the product was transformed into a bright yellow granular solid (4.8 g) which was used directly without further purification.

Intermediate 3

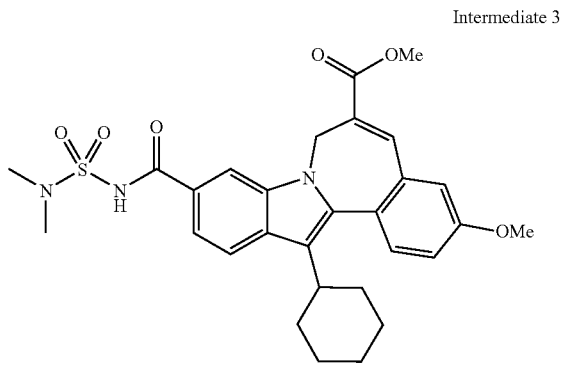

6-Carbomethoxy-13-cyclohexyl-N-[(dimethylamino)sulfonyl]-5H-indolo[2,1-a][2]benzazepine-10-carboxamide. A mixture of the 3-cyclohexyl-N-(N,N-dimethylsulfamoyl)-2-(2-formyl-4-methoxyphenyl)-H-indole-6-carboxamide (4.8 g, 0.01 mol), and cesium carbonate (7.1 g, 0.02 mol) in DMF (28 mL) was stirred for 20 hr at an oil bath temperature of 55° C. The mixture was poured into ice-water and acidified with dilute HCl to precipitate the crude product. The solid was collected, dried and flash chromatographed on $SiO_2$ (110 g) using an ethyl acetate and methylene chloride (1:10) solution containing 2% acetic acid. Homogeneous fractions were combined and evaporated to afford the title compound as a pale yellow solid (3.9 g, 71% yield). MS: 552 (M=H+).

Intermediate 4

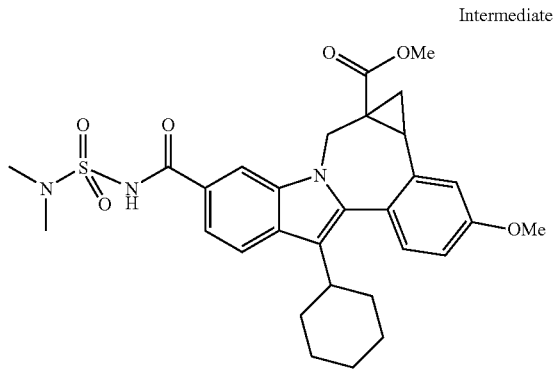

(+/−) Cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]-methyl ester. DMSO (5 mL) was added to a mixture of trimethylsulfoxonium iodide (199 mg, 0.906 mmol) and NaH (38 mg in 60% oil dispersion, 0.953 mmol) in a round-bottomed flask. The reaction mixture was stirred at rt for 0.5 hr. 7H-Indolo[2,1-a][2]benzazepine-6-carboxylic acid, 13-cyclohexyl-10-[[[(dimethylamino)sulfonyl]amino]carbonyl]-3-(methoxy)-, methyl ester (125 mg, 0.227 mmol) was then added and the reaction mixture was stirred at rt. for 3 hr., and then at 50° C. for a further 3 hr. The reaction was then quenched with water and acidified with 1N HCl solution. The crude product then precipitated as a light yellow solid which was collected by filtration and air dried, (106 mg, 83% yield). 6 mg of this material was then purified by Prep. HPLC to afford the title compound as a light yellow solid (1.8 mg). MS m/z 566 (MH+), Retention time: 3.850 min. 1H NMR (500 MHz, MeOD) δ ppm 0.28 (m, 0.36H) 1.19-2.20 (m, 11.64H) 2.70-3.02 (m, 2H) 3.03 (s, 2.16H) 3.05 (s, 3.84H) 3.49 (d, J=15.26 Hz, 0.64H) 3.54 (s, 1.92H) 3.83 (s, 1.08H) 3.91 (s, 3H) 4.08 (d, J=15.26 Hz, 0.36H) 5.29 (d, J=15.26 Hz, 0.36H) 5.50 (d, J=14.95 Hz, 0.64H) 6.98-7.06 (m, 1H) 7.16 (d, J=2.44 Hz, 0.36H) 7.23 (d, J=2.44 Hz, 0.64H) 7.30 (d, J=8.55 Hz, 0.64H) 7.34 (d, J=8.55 Hz, 0.36H) 7.56 (dd, J=8.55, 1.53 Hz, 0.64H) 7.63 (dd, J=8.55, 1.53 Hz, 0.36H) 7.88 (d, J=8.55 Hz, 0.64H) 7.91 (d, J=8.55 Hz, 0.36H) 8.12 (s, 0.36H) 8.33 (d, J=1.53 Hz, 0.64H).

Intermediate 5

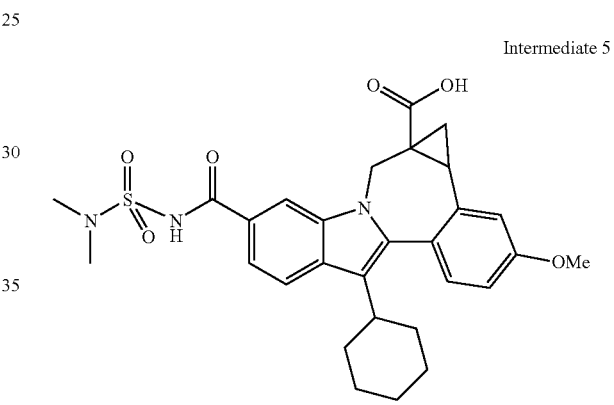

(+/−)Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy-. To a solution of (+/−)Cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]-methyl ester (100 mg, 0.177 mmol) in THF/Methanol mixture (2.0 mL/2.0 mL), 2N NaOH solution (1.0 mL) was added. The reaction mixture was heated at 90° C. under microwave conditions for 5 min. It was then concentrated, acidified with 1N HCl solution and extracted with ethyl acetate (2×20 mL). The organic layers were combined, dried ($MgSO_4$), filtered and concentrated. The residue was purified by. Prep. HPLC to afford the desired product as a light yellow solid, (59 mg, 60% yield). MS m/z 552(MH+), Retention time: 3.850 min. $^1$H NMR (300 MHz, MeOD) δ ppm 0.25 (m, 0.38H) 1.14-2.22 (m, 11.62H) 2.69-2.98 (m, 2H) 3.02 (s, 2.28H) 3.02 (s, 3.72H) 3.41 (d, J=15.00 Hz, 0.62H) 3.88 (s, 3H) 4.01 (d, J=15.00 Hz, 0.38H) 5.26 (d, J=15.00 Hz, 0.38H) 5.45 (d, J=14.64 Hz, 0.62H) 6.94-7.02 (m, 1H) 7.13 (d, J=2.56 Hz, 0.38H) 7.21 (d, J=2.20 Hz, 0.62H) 7.26 (d, J=8.42 Hz, 0.62H) 7.30 (d, J=8.78 Hz, 0.38H) 7.53 (dd, J=8.42, 1.46 Hz, 0.62H) 7.61 (dd, J=8.60, 1.65 Hz, 0.38H) 7.85 (d, J=8.42 Hz, 0.62H) 7.89 (d, J=8.42 Hz, 0.38H) 8.10 (s, 0.38H) 8.28 (d, J=1.46 Hz, 0.62H).

Intermediate 6

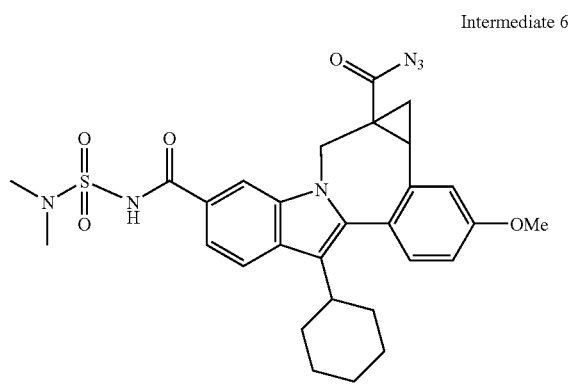

(+/−) Cycloprop[d]indolo[2,1-a][2]benzazepine-1a(2H)-carbonyl azide, 8-cyclohexyl-5-[[[(dimethylamino)sulfonyl]amino]carbonyl]-1,12b-dihydro-11-methoxy- To a mixture of the acid (+/−) Cycloprop[d]indolo[2,1-a][2]benzazepine-1a(2H)-carboxylic acid, 8-cyclohexyl-5-[[[(dimethylamino)sulfonyl]amino]carbonyl]-1,12b-dihydro-11-methoxy (1 g, 1.81 mmol) in PhMe (18 ml) at r.t. under $N_2$ was added triethylamine (0.38 ml, 2.73 mmol), followed by diphenylphosphoryl azide (DPPA) (0.59 ml, 2.73 mmol). The mixture was stirred at r.t. for 2.5 hr. The volatiles were then evaporated and the residue purified by Biotage flash chromatography (gradient elution, 0 to 60% EtOAc/Hexane) to give the product acyl azide (725.4 mg). Analytical HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=577.29, HPLC $R_t$=2.015 min. Analytical HPLC method: Solvent A=5% MeCN-95% $H_2O$-10 mM $NH_4OAc$, Solvent B=95% MeCN-5% $H_2O$-10 mM $NH_4OAc$, Start % B=0, Final % B=100, Gradient time=2 min, Flow Rate=5 ml/min, Column: Phenomenex Lina C18 5 um 3.0×50 mm; LC/MS: (ES+) m/z $(M+H)^+$=577.18, HPLC $R_t$=1.633 min.

An alternative procedure: To 1.0 g of carboxylic acid in a 100 mL round bottom flask (RBF) equipped with a septa under nitrogen, was added 20 mL of dry dichloroethane (DCE). To this solution was then added 1.2 equivalents of Diphenylphosphorylazide (DPPA) in one portion followed by 3 equivalents of triethylamine. The solution was stirred overnight at room temperature. The reaction progress was followed by an analytical Shimadzu LC/MS. The crude mixture was passed through a 24 g SiliCycle-Isco™ silica gel cartridge with DCE to give acyl azide after solvent evacuation (50-65% yield). The acyl azide was found to be stable at room temperature in a vacuum desiccator for up to three months. To a 50 mL RBF was added 0.2 mmol of acyl azide in 5.0 mL of dry toluene. The mixture was heated in an oil bath at 120° C. for 15 minutes then quickly cooled to room temperature. To this mixture was then added 3.0 equivalents of amine, and the flask was returned to the oil bath and heated at 120° C. for 60 minutes. The crude reaction mixture was then evaporated to near dryness, taken up in 1.2 mL of methanol and purified using a Shimadzu preparative HPLC employing methanol/water and 0.1% trifluoroacetic acid buffer with a Phenomenex Luna, C18, 21 mm×100 mm, 10 μm column at a gradient of 40-100% B (where A=10% HPLC grade methanol/0.1% trifluoroacetic acid/90% HPLC grade water and B=90% HPLC grade methanol/0.1% trifluoroacetic acid/10% HPLC grade water) and a flow rate of 25 mL/min. over 10 minutes with a 5-10 minute hold, to give dimethylamino sulfamide ureas 3 as yellow amorphous solids (35-50% yield). Post-purification LC/MS data was obtained on a Shimadzu analytical LC/Micromass Platform LC (ESI+) at 220 nm using the following set of conditions: Column I (Phenomenex 10 μm C18, 4.6×30 mm), Solvent system I (gradient of 0-100% B where A=10% HPLC grade methanol/0.1% trifluoroacetic acid/90% HPLC grade water and B=90% HPLC grade methanol/0.1% trifluoroacetic acid/10% HPLC grade water), in 2 minutes with a 1 minute hold at a flow rate of 5 mL/minute.

EXAMPLE 1

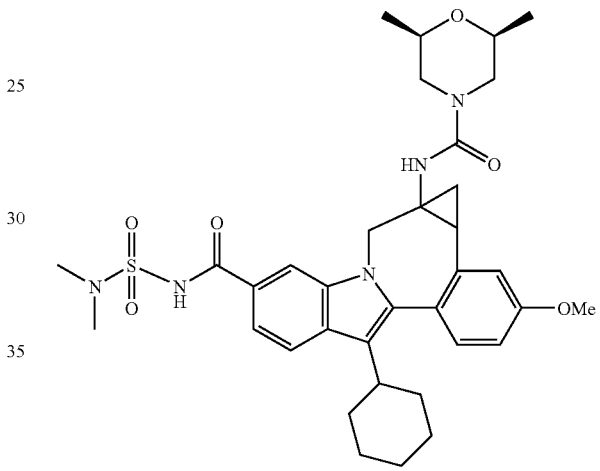

(+/−) Cycloprop[d]indolo[2,1-a][2]benzazepine-5-carboxamide, 8-cyclohexyl-N-[(dimethylamino)sulfonyl]-1a-[[[(2R,6S)-2,6-dimethyl-4-morpholinyly]carbonyl]amino]-1,1a,2,12b-tetrahydro-11-methoxy-. A mixture of the acyl azide (+/−) cycloprop[d]indolo[2,1-a][2]benzazepine-1a(2H)-carbonyl azide, 8-cyclohexyl-5-[[[(dimethylamino)sulfonyl]amino]carbonyl-]-1,12b-dihydro-11-methoxy-(42.7 mg, 74 μmol) in MeCN (2 ml) was stirred at 50° C. under $N_2$ for 1 hr. The mixture was added a solution of cis-2,6-dimethylmorpholine (30 mg, 0.26 mmol) in MeCN (0.5 ml). The reaction mixture was stirred at 50° C. for 1 hr. 15 min and then evaporated. The product urea C was isolated from the residue by preparative TLC (5% MeOH/$CH_2Cl_2$) Analytical HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Flow Rate=5 ml/min, Column: Xterra MS C18 S7 3.0×50 mm; LC/MS: (ES+) m/z $(M+H)^+$=664.45, HPLC $R_t$=1.900 min. Analytical HPLC method: Solvent A=5% MeCN-95% $H_2O$-10 mM $NH_4OAc$, Solvent B=95% MeCN-5% $H_2O$-10 mM $NH_4OAc$, Start % B=0, Final % B=100, Gradient time=2 min, Flow Rate=5 ml/min, Column: Phenomenex Lina C18 5 um 3.0×50 mm; LC/MS: (ES+) m/z $(M+H)^+$=664.38, HPLC $R_t$=1.440 min.

EXAMPLE 2

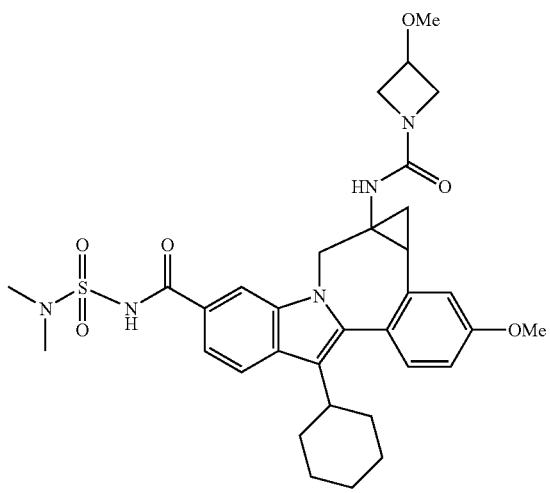

(+/−) Cycloprop[d]indolo[2,1-a][2]benzazepine-5-carboxamide, 8-cyclohexyl-N-[(dimethylamino)sulfonyl]-1,1a,2,12b-tetrahydro-11-methoxy-1a-[[(3-methoxy-1-azetidinyl)carbonyl]amino]-. A mixture of the acyl azide (+/−) cycloprop[d]indolo[2,1-a][2]benzazepine-1a(2H)-carbonyl azide, 8-cyclohexyl-5-[[[(dimethylamino)sulfonyl]amino]carbonyl]-1,12b-dihydro-11-methoxy-(98.3 mg, 0.17 mmol) in PhMe (2 ml) was stirred at 120° C. under N$_2$ for 1 hr 20 min. The mixture was added 3-methoxyazetidine hydrochloride (63.2 mg, 0.51 mmol) followed by Et$_3$N (85 µl, 0.61 ml). The reaction mixture was stirred at 120° C. for 30 min and then evaporated. The residue was purified by preparative TLC (5% MeOH/CH$_2$Cl$_2$) to give the product. Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=636.46, HPLC R$_t$=1.878 min. Analytical HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=636.31, HPLC R$_t$=1.363 min.

EXAMPLE 3

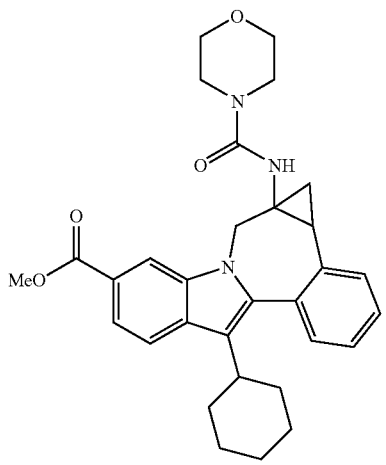

(+/−)Cycloprop[d]indolo[2,1-a][2]benzazepine-5-carboxylic acid, 8-cyclohexyl-1,1a,2,12b-tetrahydro-1a-[(4-morpholinylcarbonyl)amino]-, methyl ester. To a solution of cycloprop[d]indolo[2,1-a][2]benzazepine-1a,5(2H)-dicarboxylic acid, 8-cyclohexyl-1,12b-dihydro, 5-methyl ester (112 mg, 0.261 mmol) in CH$_2$Cl$_2$ (5 mL), triethyl amine (0.109 mL, 0.783 mmol) and DPPA (0.067 mL, 0.313 mmol) were added. The reaction mixture was stirred at rt. for overnight. Then the reaction mixture went through a Biotage column and washed with CH$_2$Cl$_2$. The fractions were collected and concentrated. The residue was then dissolved in toluene (4 mL) and morpholine (0.034 mL, 0.392 mmol) was added. The reaction mixture was heated at 100° C. under microwave condition for 30 min. Toluene was evaporated and methanol was added. A white solid was collected as pure compound. (98 mg, 73% yield). MS m/z 514(MH$^+$), Retention time: 3.875 min. 1H NMR (500 MHz, DMSO-D6) δ ppm −0.06 (m, 0.62H) 0.84 (m, 0.62H) 1.07-2.15 (m, 10.76H) 2.29-2.35 (m, 1H) 2.66-2.78 (m, 0.38H) 2.90-2.99 (m, 2H) 3.10-3.19 (m, 1.62H) 3.24-3.44 (m, 4H) 3.53-3.60 (m, 1.62H) 3.87 (s, 1.86H) 3.89 (s, 1.14H) 4.18 (d, J=14.65 Hz, 0.38H) 4.77 (d, J=14.34 Hz, 0.38H) 5.22 (d, J=15.26 Hz, 0.62H) 6.59 (s, 0.62H) 7.30-7.49 (m, 3.38H) 7.52-7.58 (m, 1H) 7.61 (dd, J=8.55, 1.53 Hz, 0.62H) 7.66 (dd, J=8.39, 1.37 Hz, 0.38H) 7.87-7.94 (m, 1.62H) 8.21 (s, 0.38H).

EXAMPLE 4

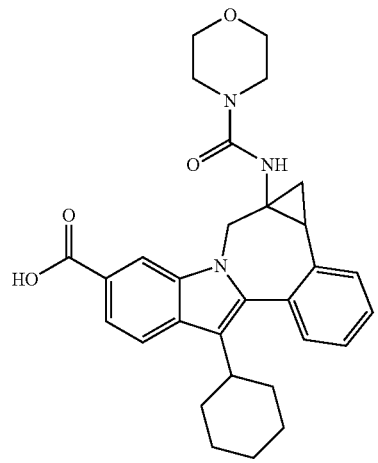

(+/−) Cycloprop[d]indolo[2,1-a][2]benzazepine-5-carboxylic acid, 8-cyclohexyl-1,1a,2,12b-tetrahydro-1a-[(4-morpholinylcarbonyl)amino]-. To a mixture of (+/−) Cycloprop[d]indolo[2,1-a][2]benzazepine-5-carboxylic acid, 8-cyclohexyl-1,1a,2,12b-tetrahydro-1a-[(4-morpholinylcarbonyl)amino]-, methyl ester (40 mg, 0.078 mmol) and potassium trimethylsilanolate (50 mg, 0.389 mmol) in a round-bottomed flask, THF (5 mL) was added. The reaction mixture was stirred t rt. for 8 hr. Then it was acidified with 1N HCl solution and extracted with ethyl acetate. The organic layer was separated, dried (MgSO$_4$) and concentrated. The residue was then purified by Prep.HPLC column to give a light yellow solid as final compound. (15 mg, 44% yield). MS m/z 500 (MH$^+$), Retention time: 3.721 min. 1H NMR (500 MHz, DMSO-D6) δ ppm −0.03 (m, 0.4H) 0.84 (m, 0.4H) 1.05-2.16 (m, 11H) 2.24-2.34 (m, 1H) 2.67-2.79 (m, 0.6H) 2.84-2.98 (m, 2H) 3.08-3.18 (m, 1.4H) 3.21-3.64 (m, 5.6H) 4.17 (d, J=14.34 Hz, 0.4H) 4.75 (d, J=14.34 Hz, 0.4H) 5.20 (d, J=14.95 Hz, 0.6H) 6.57 (s, 0.6H) 7.29-7.49 (m, 3.4H) 7.51-7.58 (m, 1H) 7.60 (d, J=8.55 Hz, 0.6H) 7.65 (d, J=8.55 Hz, 0.4H) 7.87 (m, 1H) 7.91 (s, 0.6H) 8.18 (s, 0.4H).

EXAMPLE 5

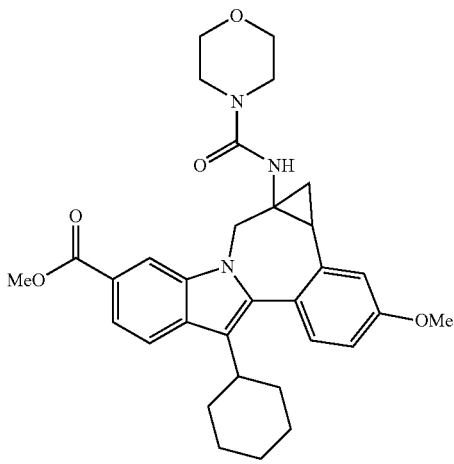

(+/−) Cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]-, methyl ester. To a solution of cycloprop[d]indolo[2,1-a][2]benzazepine-1a,5 (2H)-dicarboxylic acid, 8-cyclohexyl-1,12b-dihydro-11-methoxy-, 5-methyl ester (105 mg, 0.228 mmol) in CH$_2$Cl$_2$ (5 mL), triethyl amine (0.095 mL, 0.684 mmol) and DPPA (0.059 mL, 0.274 mmol) were added. The reaction mixture was stirred at rt. for 2 hr. Then the reaction mixture went through a Biotage column and washed with CH$_2$Cl$_2$. The fractions were collected and concentrated. The residue was then dissolved in toluene (4 mL) and morpholine (0.030 mL, 0.342 mmol) was added. The reaction mixture was heated at 100° C. under microwave condition for 30 min. Toluene was evaporated and methanol was added. A white solid was collected as pure compound. (48 mg, 39% yield). MS m/z 544 (MH$^+$), Retention time: 3.891 min. 1H NMR (500 MHz, DMSO-D6) δ ppm −0.03 (m, 0.38H) 0.73-0.94 (m, 0.62H) 1.05-2.16 (m, 11H) 2.25-2.35 (m, 1H) 2.67-2.80 (m, 0.38H) 2.82-3.01 (m, 2H) 3.09-3.20 (m, 1.38H) 3.23-3.49 (m, 4.24H) 3.51-3.67 (m, 1.62H) 3.83-3.91 (m, 6H) 4.19 (d, J=14.04 Hz, 0.38H) 4.76 (d, J=14.65 Hz, 0.38H) 5.22 (d, J=14.95 Hz, 0.62H) 6.60 (s, 0.62H) 6.99 (dd, J=8.55, 2.44 Hz, 0.38H) 7.05 (dd, J=8.39, 2.59 Hz, 0.62H) 7.11 (d, J=2.44 Hz, 0.62H) 7.15 (d, J=2.44 Hz, 0.38H) 7.24-7.34 (m, 1H) 7.44 (s, 0.38H) 7.61 (d, J=8.54 Hz, 0.62H) 7.66 (d, J=8.55 Hz, 0.38H) 7.88 (d, J=8.55 Hz, 1H) 7.90 (s, 0.62H) 8.20 (s, 0.38H).

EXAMPLE 6

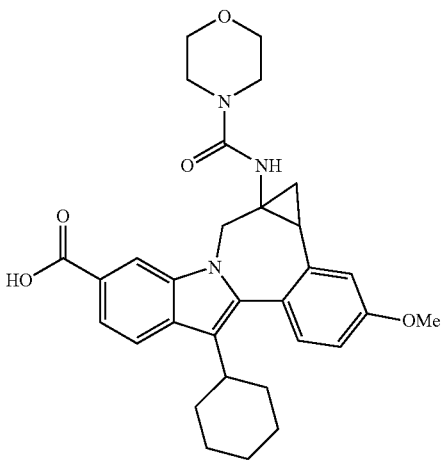

(+/−) Cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]-. To a mixture of (+/−) cycloprop[d]indolo[2,1-a][2]benzazepine-5-carboxylic acid, 8-cyclohexyl-1,1a,2,12b-tetrahydro-11-methoxy-1a-[(4-morpholinylcarbonyl)amino]-, methyl ester (43 mg, 0.079 mmol) and potassium trimethylsilanolate (51 mg, 0.395 mmol) in a round-bottomed flask, THF (5 mL) was added. The reaction mixture was stirred at rt. overnight. Then it was acidified with 1N HCl solution and extracted with ethyl acetate. The organic layer was separated, dried (MgSO$_4$) and concentrated. The residue was then purified by Prep.HPLC column to give the product as a light yellow solid, (10 mg, 24% yield). MS m/z 530(MH$^+$), Retention time: 3.733 min. 1H NMR (300 MHz, DMSO-D6) δ ppm −0.04 (m, 0.38H) 0.81 (m, 0.62H) 0.96-2.15 (m, 11H) 2.19-2.34 (m, 1H) 2.66-2.78 (m, 0.38H) 2.80-2.99 (m, 2H) 3.01-3.61 (m, 7.24H) 3.83 (s, 1.14H) 3.85 (s, 1.86H) 4.15 (d, J=14.27 Hz, 0.38H) 4.71(d, J=13.90 Hz, 0.38H) 5.17 (d, J=15.37 Hz, 0.62H) 6.58 (s, 0.62H) 6.91-7.15 (m, 2H) 7.20-7.32 (m, 1H) 7.42 (s, 0.38H) 7.57 (d, J=8.41 Hz, 0.62H) 7.62 (d, J=8.79 Hz, 0.38H) 7.83 (d, J=8.42 Hz, 1H) 7.87 (s, 0.62H) 8.14 (s, 0.38H) 12.52 (s, 1H).

EXAMPLE 7

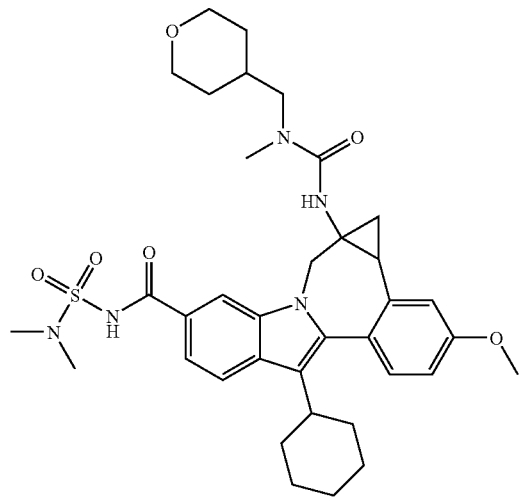

8-Cyclohexyl-N-(dimethylsulfamoyl)-11-methoxy-1a-((methyl(tetrahydro-2H-pyran-4-ylmethyl)carbamoyl)amino)-1,1a,2,12b-tetrahydrocyclopropa[d]indolo[2,1-a][2]benzazepine-5-carboxamide. 1H NMR (500 MHz, CD$_3$OD) δ ppm: 0.17 (m, 0.25H), 0.83-0.95 (m, 0.75H), 1.22 (m, 4H), 1.44 (m, 3H), 1.68 (m, 1H), 1.79 (m, 2H), 1.93 (m, 1H), 1.99 (m, 1H), 2.09 (m, 2H), 2.35 (m, 1H), 2.62 (m, 2H), 2.79 (m, 1H), 2.85 (m, 1H), 2.92 (m, 1H), 2.99 (s, 6H), 3.00 (s, 3H), 3.17 (m, 2H), 3.40 (m, 1H), 3.74 (m, 1H), 3.86 (s, 3H), 3.88 (m, 1H), 5.23 (d, J=14.65 Hz, 1H), 6.96 (m, 1H), 7.10-7.17 (m, 1H), 7.26-7.30 (m, 1H), 7.55-7.58 (m, 1H), 7.84-7.90 (m, 1H), 7.94-8.09 (m, 1H). LC/MS: m/z 678.25 (MH$^+$), Rf 2.07 min., 100% purity.

EXAMPLE 8

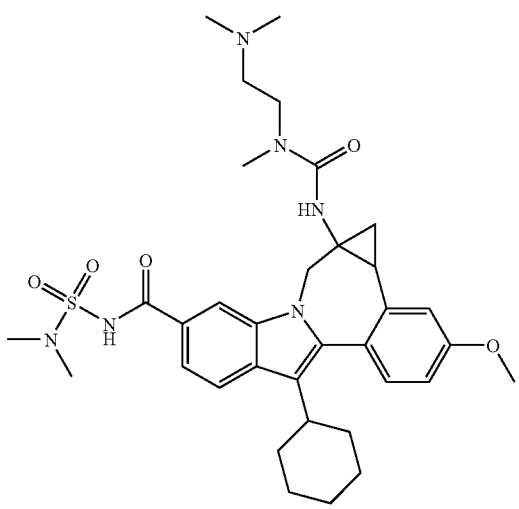

8-Cyclohexyl-1a-(((2-(dimethylamino)ethyl) (methyl) carbamoyl)amino)-N-(dimethylsulfamoyl)-11-methoxy-1, 1a,2,12b-tetrahydrocyclopropa[d]indolo[2,1-a][2]benzazepine-5-carboxamide. $^1$H NMR (500 MHz, CD$_3$OD) δ ppm: 0.08 (m, 0.20H), 0.78 (m, 0.20H), 1.20 (m, 0.8H), 1.27 (m, 0.8H), 1.40 (m, 2H), 1.66 (m, 1H), 1.76 (m, 1H), 1.88-1.96 (m, 2H), 2.05 (m, 2H), 2.26 (m, 1H), 2.37 (s, 3H), 2.81 (s, 1H), 2.92 (s, 5H), 2.95 (s, 6H), 3.30 (m, 3H), 3.15 (m, 1H), 3.33 (m, 1H), 3.38-3.41 (m, 1H), 3.46 (m, 1H), 3.62 (m, 1H), 3.82 (s, 3H), 5.18 (d, J=14.65 Hz, 1H), 6.95 (dd, J=8.55, 1.83 Hz, 1H), 7.08 (d, J=1.83 Hz, 1H), 7.27 (m, 1H), 7.50 (dd, J=8.54, 1.53 Hz, 1H), 7.81-7.86 (m, 2H). LC/MS: m/z 651.19 (MH$^+$), Rf 1.83 min., 98.6% purity.

EXAMPLE 9

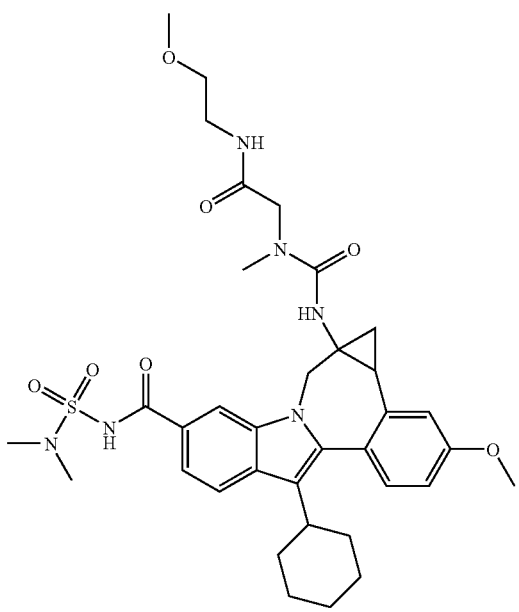

8-Cyclohexyl-N-(dimethylsulfamoyl)-11-methoxy-1a-(((2-((2-methoxyethyl)amino)-2-oxoethyl)(methyl)carbamoyl)amino)-1,1a,2,12b-tetrahydrocyclopropa[d]indolo[2,1-a][2]benzazepine-5-carboxamide. $^1$H NMR (500 MHz, CD$_3$OD) δ ppm: 0.17 (t, J=6.41 Hz, 0.25H), 0.86 (m, 0.25H), 1.22 (m, 0.75H), 1.28 (m, 1H), 1.35 (m, 0.75H), 1.44 (m, 2H), 1.70 (m, 1H), 1.80 (m, 2H), 1.93 (m, 1H), 2.01 (m, 1H), 2.10 (m, 2H), 2.29 (m, 0.75H), 2.35 (m, 0.25H), 2.93 (m, 2H), 2.99 (m, 1H), 3.01 (s, 6H), 3.33 (m, 2H), 3.37 (m, 2H), 3.44 (m, 3H), 3.58 (d, J=16.79 Hz, 1H), 3.85 (s, 2.25H), 3.88 (s, 0.75H), 3.95 (m, 2H), 4.03 (m, 1H), 5.13 (d, J=14.65 Hz, 1H), 6.92 (dd, J=8.55, 1.83 Hz, 0.25H), 6.98 (dd, J=8.55, 1.83 Hz, 0.75H), 7.13 (m, 1H), 7.30 (m, 1H), 7.56 (m, 1H), 7.85-7.89 (m, 1H), 7.97 (s, 0.75H), 8.11 (s, 0.25H). LC/MS: m/z 695.27 (MH$^+$), Rf 2.05 min., 95.0% purity.

EXAMPLE 10

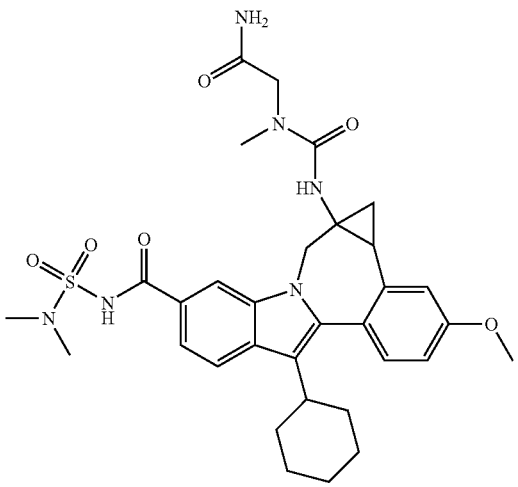

1a-(((2-Amino-2-oxoethyl)(methyl)carbamoyl)amino)-8-cyclohexyl-N-(dimethylsulfamoyl)-11-methoxy-1,1a,2,12b-tetrahydrocyclopropa[d]indolo[2,1-a][2]benzazepine-5-carboxamide. $^1$H NMR (500 MHz, CD$_3$OD) δ ppm: 0.16 (t, J=6.40 Hz, 0.20H), 0.88 (m, 0.20H), 1.21 (t, J=6.40 Hz, 0.8H), 1.28 (m, 1H), 1.30 (m, 0.8H), 1.45 (m, 2H), 1.81 (m, 3H), 1.97 (m, 2H), 2.13 (m, 2H), 2.36 (m, 1H), 2.59 (s, 2H), 2.86-2.95 (m, 1H), 3.30 (s, 6H), 3.42 (d, J=14.95 Hz, 1H), 3.61 (d, J=17.09 Hz, 1H), 3.86 (s, 2.40H), 3.88 (s, 0.60H), 3.97 (m, 1H), 4.22 (m, 1H), 5.10 (d, J=14.95 Hz, 1H), 6.91 (dd, J=8.55, 2.75 Hz, 0.20H), 6.95 (dd, J=8.55, 2.75 Hz, 0.80H), 7.13 (m, 1H), 7.28 (m, 1H), 7.58 (m, 1H), 7.85-7.90 (m, 1H), 7.96 (m, 0.80H), 8.11 (s, 0.20H). LC/MS: m/z 637.16 (MH$^+$), Rf 2.04 min., 95.0% purity.

EXAMPLE 11

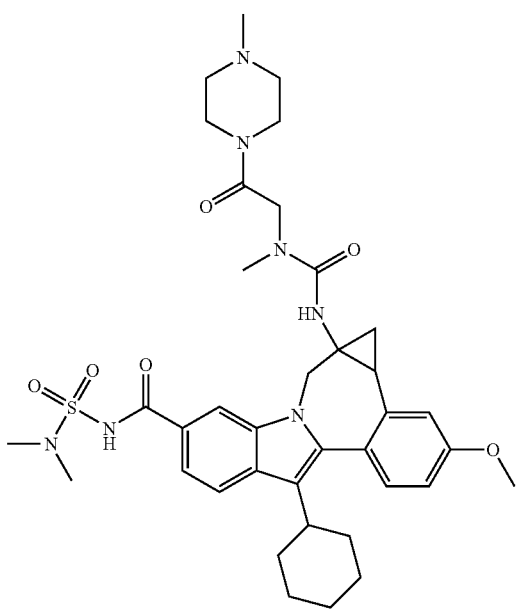

8-Cyclohexyl-N-(dimethylsulfamoyl)-11-methoxy-1a-((methyl(2-(4-methyl-1-piperazinyl)-2-oxoethyl)carbamoyl)amino)-1,1a,2,12b-tetrahydrocyclopropa[d]indolo[2,1-a][2]benzazepine-5-carboxamide. $^1$H NMR (500 MHz, CD$_3$OD) δ ppm: 0.15 (m, 0.20H), 0.84 (m, 0.20H), 1.22 (t, J=5.90 Hz, 0.8H), 1.28 (m, 1H), 1.34 (m, 0.8H), 1.46 (m, 2H), 1.70 (m, 1H), 1.80 (m, 2H), 1.92-1.99 (m, 2H), 2.10 (m, 2H), 2.29 (m, 0.8H), 2.36 (m, 0.2H), 2.48 (s, 2H), 2.85 (m, 1H), 2.92-3.03 (m, 12H), 3.07 (m, 2H), 3.44 (d, J=14.95 Hz, 1H), 3.54 (m, 2H), 3.86 (m, 2.40H), 3.88 (m, 0.60H), 3.92 (m, 1H), 4.07 (m, 1H), 4.19 (m, 1H), 4.29 (m, 1H), 5.13 (d, J=14.95 Hz, 1H), 6.93 (m, 0.20H), 6.97 (m, 0.80H), 7.12 (m, 1H), 7.29 (m, 1H), 7.55-7.61 (m, 1H), 7.84-7.89 (m, 1H), 8.02 (s, 0.80H), 8.10 (s, 0.20H). LC/MS: m/z 720.18 (MH$^+$), Rf 1.87 min., 97.8% purity.

Examples 12-17 use the general methods below. Analytical HPLC and LC/MS were performed by using Shimadzu-VP instrument with UV detection at 220 nm and Waters Micromass. Biotage Horizon was used for flash chromatography as indicated.

EXAMPLE 12

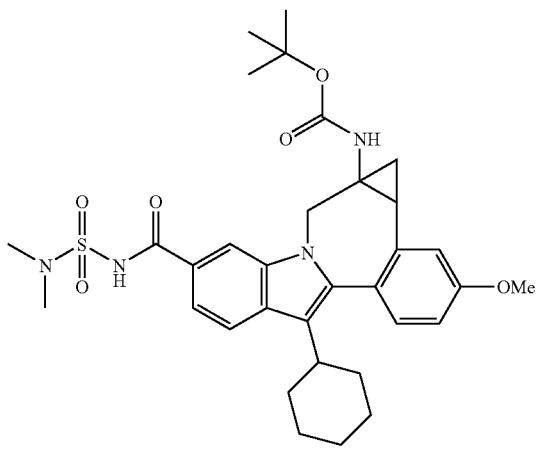

1,1-Dimethylethyl (8-cyclohexyl-5-((((dimethylamino)sulfonyl)amino)carbonyl)-11-(methyloxy)-1,12b-dihydrocyclopropa[d]indolo[2,1-a][2]benzazepin-1a(2H)-yl)carbamate. A mixture of the azide, 8-cyclohexyl-5-((((dimethylamino)sulfonyl)carbamoyl)-11-methoxy-1,12b-dihydrocyclopropa[d]indolo[2,1-a][2]benzazepine-1a(2H)-carbonyl azide, (102 mg) in PhMe (2 ml) under N$_2$ was stirred at 120° C. for 1 hr. 35 min., cooled to r.t. and then concentrated. The residue was added tert-butanol (2 ml) and stirred at 120° C. for 1 hr. 45 min., and then evaporated. The crude product was purified by flash chromatography (gradient elution 0-60% EtOAc/Hexane) to give (BMS-792039) 1,1-dimethylethyl (8-cyclohexyl-5-((((dimethylamino)sulfonyl)amino)carbonyl)-11-(methyloxy)-1,12b-dihydrocyclopropa[d]indolo[2,1-a][2]benzazepin-1a(2H)-yl)carbamate as a pale yellow solid. Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=623.45, HPLC R$_f$=1.957 min. Analytical HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=623.37, HPLC R$_f$=1.628 min.

EXAMPLE 13

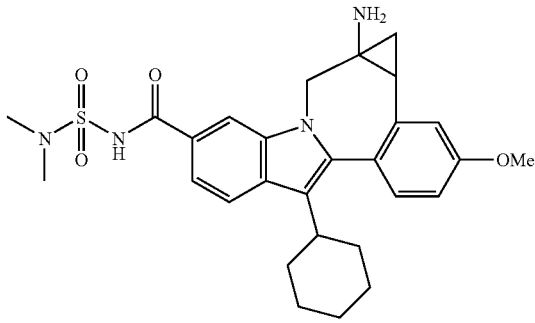

1a-Amino-8-cyclohexyl-N-((dimethylamino)sulfonyl)-11-(methyloxy)-1,1a,2,12b-tetrahydrocyclopropa[d]indolo[2,1-a][2]benzazepine-5-carboxamide. To 1,1-dimethylethyl (8-cyclohexyl-5-((((dimethylamino)sulfonyl)amino)carbonyl)-11-(methyloxy)-1,12b-dihydrocyclopropa[d]indolo[2,1-a][2]benzazepin-1a(2H)-yl)carbamate (75.3 mg) at r.t. under N$_2$ was added a solution of HCl in 1,4-dioxane (0.5 ml, 4M). The mixture was stirred for 3 hr. 35 min., evaporated to give the hydrochloride salt of 1a-amino-8-cyclohexyl-N-((dimethylamino)sulfonyl)-11-(methyloxy)-1,1a,2,12b-tetrahydrocyclopropa[d]indolo[2,1-a][2]benzazepine-5-carboxamide, which was used without further purification. Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=523.39, HPLC R$_f$=1.632 min.

EXAMPLE 14

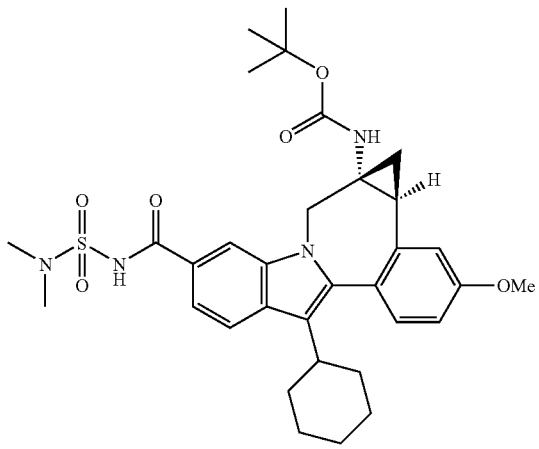

tert-Butyl((1aR,12bS)-8-cyclohexyl-5-((dimethylsulfamoyl)carbamoyl)-11-methoxy-1,12b-dihydrocyclopropa[d]indolo[2,1-a][2]benzazepin-1a(2H)-yl)carbamate. tert-Butyl ((1aR,12bS)-8-cyclohexyl-5-((dimethylsulfamoyl) carbamoyl)-11-methoxy-1,12b-dihydrocyclopropa[d]indolo[2,1-a][2]benzazepin-1a(2H)-yl)carbamate was prepared from the corresponding chiral acid, (aR,12bS)-8-cyclohexyl-5-((dimethylsulfamoyl)carbamoyl)-11-methoxy-1,12b-dihydrocyclopropa[d]indolo[2,1-a][2]benzazepine-1a(2H)-carboxylic acid, in a similar manner as described above. Analytical HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)=623.16, HPLC $R_t$=1.980 min. Analytical HPLC method: Solvent A=5% MeCN-95% $H_2O$-10 mM $NH_4OAc$, Solvent B=95% MeCN-5% $H_2O$-10 mM $NH_4OAc$, Start % B=0, Final % B=100, Gradient time=2 min, Flow Rate=5 ml/min, Column: Phenomenex Lina C18 5 um 3.0×50 mm; LC/MS: (ES+) m/z (M+H)$^+$=623.48, HPLC $R_t$=1.600 min. Average specific rotation=−56.55° (1.29 mg/ml in MeOH; Wavelength 589 nm; 100 mm cell).

EXAMPLE 15

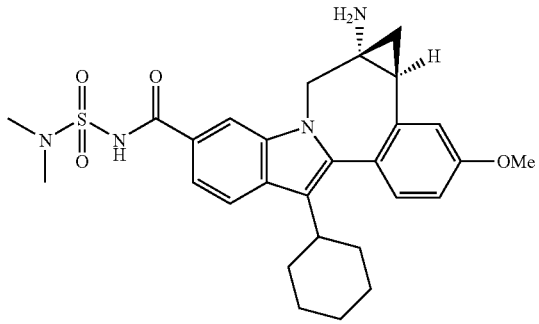

(1aR,12bS)-1a-Amino-8-cyclohexyl-N-(dimethylsulfamoyl)-11-methoxy-1,1a,2,12b-tetrahydrocyclopropa[d]indolo[2,1-a][2]benzazepine-5-carboxamide. The hydrochloride salt of (1aR,12bS)-1a-amino-8-cyclohexyl-N-(dimethylsulfamoyl)-11-methoxy-1,1a,2,12b-tetrahydrocyclopropa[d]indolo[2,1-a][2]benzazepine-5-carboxamide was prepared from (BMS-807598) tert-butyl ((1aR,12bS)-8-cyclohexyl-5-((dimethylsulfamoyl)carbamoyl)-11-methoxy-1,12b-dihydrocyclopropa[d]indolo[2,1-a][2]benzazepin-1a(2H)-yl)carbamate in a similar manner as described above. Analytical HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)=523.26, HPLC $R_t$=1.640 min. Average specific rotation=−36.95° (1.19 mg/ml in MeOH; Wavelength 589 nm; 50 mm cell).

EXAMPLE 16

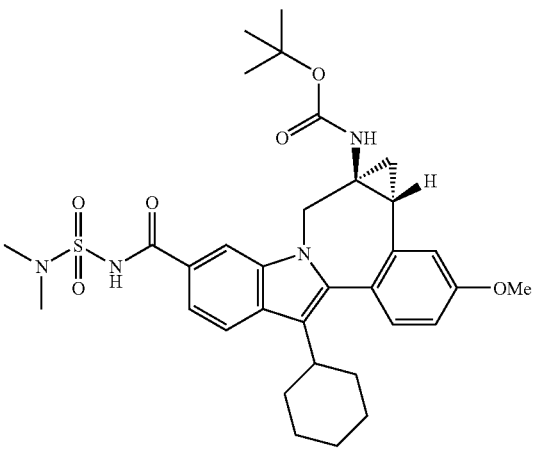

tert-Butyl((1aS,12bR)-8-cyclohexyl-5-((dimethylsulfamoyl)carbamoyl)-11-methoxy-1,12b-dihydrocyclopropa[d]indolo[2,1-a][2]benzazepin-1a(2H)-yl)carbamate. tert-Butyl ((1aS,12bR)-8-cyclohexyl-5-((dimethylsulfamoyl)carbamoyl)-11-methoxy-1,12b-dihydrocyclopropa[d]indolo[2,1-a][2]benzazepin-1a(2H)-yl)carbamate was prepared from the corresponding chiral acid, (1aS,12bR)-8-cyclohexyl-5-((dimethylsulfamoyl)carbamoyl)-11-methoxy-1,12b-dihydrocyclopropa[d]indolo[2,1-a][2]benzazepine-1a(2H)-carboxylic acid, in a similar manner as described above. Analytical HPLC method: Solvent A=10% MeOH-90% $H_2O$-0.1% TFA, Solvent B=90% MeOH-10% $H_2O$-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=623.10, HPLC $R_t$=1.935 min. Analytical HPLC method: Solvent A=5% MeCN-95% $H_2O$-10 mM $NH_4OAc$, Solvent B=95% MeCN-5% $H_2O$-10 mM $NH_4OAc$, Start % B=0, Final % B=100, Gradient time=2 min, Flow Rate=5 ml/min, Column: Phenomenex Lina C18 5 um 3.0×50 mm; LC/MS: (ES−) m/z (M−H)$^+$=621.26, HPLC $R_t$=1.653 min. Average specific rotation=+56.07° (2.57 mg/ml in MeOH; Wavelength 589 nm; 50 mm cell).

EXAMPLE 17

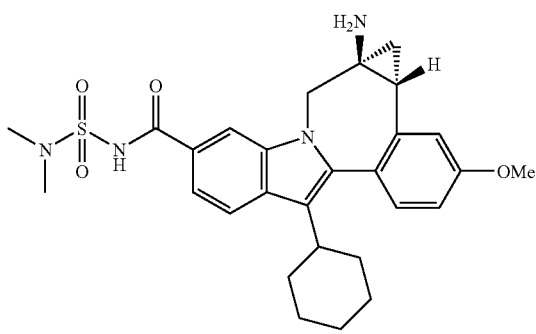

(1aS,12bR)-1a-Amino-8-cyclohexyl-N-(dimethylsulfamoyl)-11-methoxy-1,1a,2,12b-tetrahydrocyclopropa[d]indolo[2,1-a][2]benzazepine-5-carboxamide. The hydrochloride salt of (1aS,12bR)-1a-Amino-8-cyclohexyl-N-(dimethylsulfamoyl)-11-methoxy-1,1a,2,12b-tetrahydrocyclopropa[d]indolo[2,1-a][2]benzazepine-5-carboxamide was prepared from tert-butyl((1aS,12bR)-8-cyclohexyl-5-((dimethylsulfamoyl)carbamoyl)-11-methoxy-1,12b-dihydrocyclopropa[d]indolo[2,1-a][2]benzazepin-1a(2H)-yl)carbamate in a similar manner as described above. Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)=523.32, HPLC R$_t$=1.603 min.

EXAMPLE 18

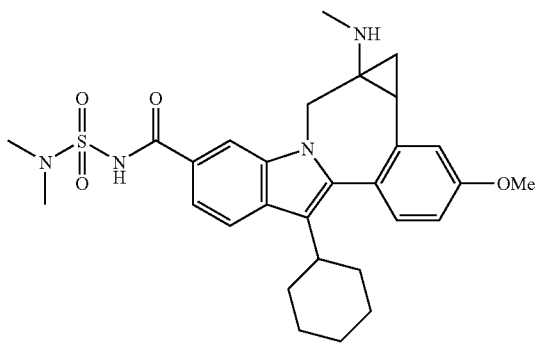

8-Cyclohexyl-N-(dimethylsulfamoyl)-11-methoxy-1a-(methylamino)-1,1a,2,12b-tetrahydrocyclopropa[d]indolo[2,1-a][2]benzazepine-5-carboxamide. The hydrochloride salt of 8-cyclohexyl-N-(dimethylsulfamoyl)-11-methoxy-1a-(methylamino)-1,1a,2,12b-tetrahydrocyclopropa[d]indolo[2,1-a][2]benzazepine-5-carboxamide was prepared from 1,1-dimethylethyl (8-cyclohexyl-5-((((dimethylamino)sulfonyl)amino)carbonyl)-11-(methyloxy)-1,12b-dihydrocyclopropa[d]indolo[2,1-a][2]benzazepin-1a(2H)-yl)carbamate in two steps (MeI, NaH, DMF, r.t. followed by HCl, 1,4-dioxane, r.t.) Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=537.12, HPLC R$_t$=1.627 min. Analytical HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Flow Rate=5 ml/min, Column: Phenomenex Luna C18 5 um 3.0×50 mm; LC/MS: (ES+) m/z (M+H)$^+$=537.55, HPLC R$_t$=1.392 min.

EXAMPLE 19

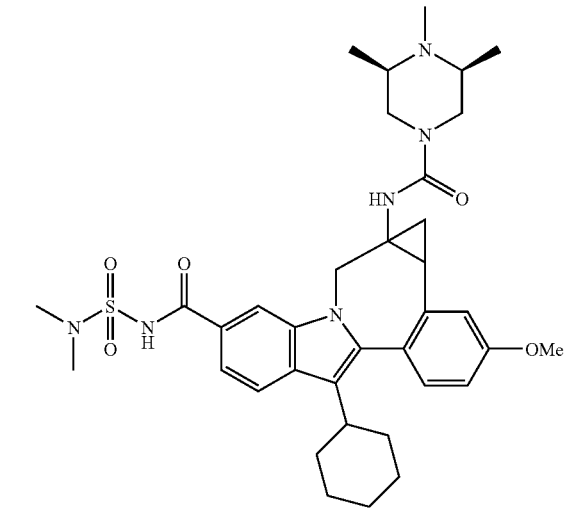

8-Cyclohexyl-N-((dimethylamino)sulfonyl)-11-methoxy-1a-((((3R,5S)-3,4,5-trimethyl-1-piperazinyl)carbonyl)amino)-1,1a,2,12b-tetrahydrocyclopropa[d]indolo[2,1-a][2]benzazepine-5-carboxamide. A mixture of the acyl azide, 8-cyclohexyl-5-(((dimethylamino)sulfonyl)carbamoyl)-11-methoxy-1,12b-dihydrocyclopropa[d]indolo[2,1-a][2]benzazepine-1a(2H)-carbonyl azide, (98 mg, 0.17 mmol) in PhMe (2 ml) was stirred at 120° C. under N$_2$ for 1 hr 30 min. The mixture was added 1,2,6-trimethylpiperazine bistrifluoroacetic acid salt (182 mg, 0.51 mmol) followed by Et$_3$N (170 µl, 1.22 mmol). The reaction mixture was stirred at 120° C. for 30 min and then evaporated. The residue was purified by Shimadzu-VP preparative reverse phase HPLC with separation method: Solvent A=10% MeOH-90% H$_2$O-0.1% TFA, Solvent B=90% MeOH-10% H$_2$O-0.1% TFA, Start % B=0, Final % B=100, Gradient time=6 min, Flow Rate=30 mL/min, Column: Xterra Prep MS C18 5u 30×50 mm, Fraction Collection: 6.31-6.70 min. (UV detection at 220 nm) to give the trifluoroacetic acid salt of the compound of Example 19,8-cyclohexyl-N-((dimethylamino)sulfonyl)-11-methoxy-1a-((((3R,5S)-3,4,5-trimethyl-1-piperazinyl)carbonyl)amino)-1,1a,2,12b-tetrahydrocyclopropa[d]indolo[2,1-a][2]benzazepine-5-carboxamide, (56.3 mg) as a light yellow solid. Analytical HPLC method: Solvent A=10% MeOH-90% H$_2$O-0.1% TFA, Solvent B=90% MeOH-10% H$_2$O-0.1% TFA, Start % B=0, Final % B=100, Gradient time=2 min, Flow Rate=5 ml/min, Column: Xterra MS C18 S7 3.0×50 mm; LC/MS: (ES+) m/z (M+H)$^+$=677.56, HPLC R$_t$=1.703 min. Analytical HPLC method: Solvent A=5% MeCN-95% H$_2$O-10 mM NH$_4$OAc, Solvent B=95% MeCN-5% H$_2$O-10 mM NH$_4$OAc, Start % B=0, Final % B=100, Gradient time=2 min, Flow Rate=5 ml/min, Column: Phenomenex Luna C18 5 um 3.0×50 mm; LC/MS: (ES+) m/z (M+H)$^+$=677.37, HPLC R$_t$=1.247 min.

We claim:
1. A compound of formula I

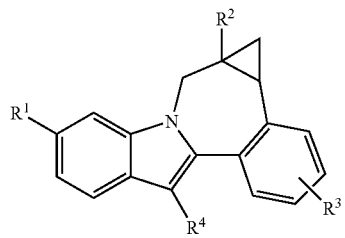

where:
R$^1$ is CO$_2$R$^5$ or CONR$^6$R$^7$;
R$^2$ is N(R$^{10}$)(R$^{11}$);
R$^3$ is hydrogen, halo, alkyl, alkenyl, hydroxy, benzyloxy, alkoxy, or haloalkoxy;
R$^4$ is cycloalkyl;
R$^5$ is hydrogen or alkyl;
R$^6$ is hydrogen, alkyl, alkylSO$_2$, cycloalkylSO$_2$, haloalkylSO$_2$, (R$^7$)(R$^8$)NSO$_2$, or (R$^9$)SO$_2$;
R$^7$ is hydrogen or alkyl;
R$^8$ is hydrogen or alkyl;
R$^9$ is azetidinyl, pyrrolidinyl, piperidinyl, piperazinyl, morpholinyl, thiomorpholinyl, homopiperidinyl, or homomorpholinyl, and is substituted with 0-3 substituents selected from alkyl and alkoxy;
R$^{10}$ is hydrogen, alkyl, alkoxyCO, or (R$^{12}$)(R$^{13}$)NCO;
R$^{11}$ is hydrogen or alkyl;
R$^{12}$ is hydrogen, alkyl, alkoxyalkyl, aminoalkyl, (alkylamino)alkyl, (dialkylamino)alkyl, (CO$_2$R$^{14}$)alkyl, (CON(R$^{15}$)(R$^{16}$))alkyl, or (tetrahydropyranyl)alkyl;
R$^{13}$ is hydrogen, alkyl, alkoxyalkyl, aminoalkyl, (alkylamino)alkyl, or (dialkylamino)alkyl;
or (R$^{12}$)(R$^{13}$)N taken together is azetidinyl, pyrrolidinyl, piperidinyl, piperazinyl, morpholinyl, thiomorpholinyl, homopiperidinyl, or homomorpholinyl and is substituted with 0-3 substituents selected from alkyl and alkoxy;
R$^{14}$ is hydrogen or alkyl;
R$^{15}$ is hydrogen or alkyl; and
R$^{16}$ is hydrogen or alkyl; or
N(R$^{15}$)(R$^{16}$) taken together is azetidinyl, pyrrolidinyl, piperidinyl, piperazinyl, morpholinyl, thiomorpholinyl, homopiperidinyl, or homomorpholinyl and is substituted with 0-3 substituents selected from alkyl and alkoxy;
or a pharmaceutically acceptable salt thereof.

2. A compound of claim 1 where R$^1$ is CONHR$^6$ and R$^6$ is alkylSO$_2$, cycloalkylSO$_2$, haloalkylSO$_2$, (R$^7$)(R$^8$)NSO$_2$, or (R$^9$)SO$_2$.

3. A compound of claim 1 where R$^3$ is hydrogen.

4. A compound of claim 1 where R$^3$ methoxy.

5. A compound of claim 1 where R$^4$ is cyclohexyl.

6. A compound of claim 1 where R$^6$ is (R$^7$)(R$^8$)NSO$_2$ or (R$^9$)SO$_2$.

7. A compound of claim 1 where R$^{10}$ is (R$^{12}$)(R$^{13}$)NCO.

8. A compound of claim 1 where R$^{12}$ is alkoxyalkyl, (dialkylamino)alkyl, (CON(R$^{15}$)(R$^{16}$))alkyl, or (tetrahydropyranyl)alkyl.

9. A compound of claim 1 where (R$^{12}$)(R$^{13}$)N taken together is azetidinyl, pyrrolidinyl, piperidinyl, piperazinyl, morpholinyl, thiomorpholinyl, homopiperidinyl, or homomorpholinyl and is substituted with 0-3 substituents selected from alkyl and alkoxy.

10. A compound of claim 1 according to the following stereochemistry:

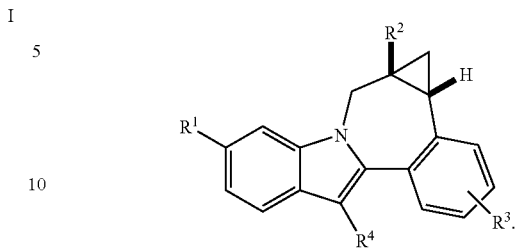

11. A compound of claim 1 according to the following stereochemistry:

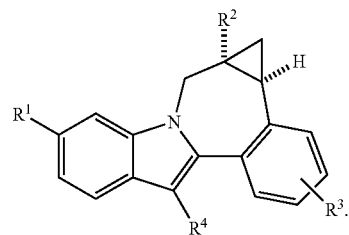

12. A compound of claim 1 selected from the group consisting of

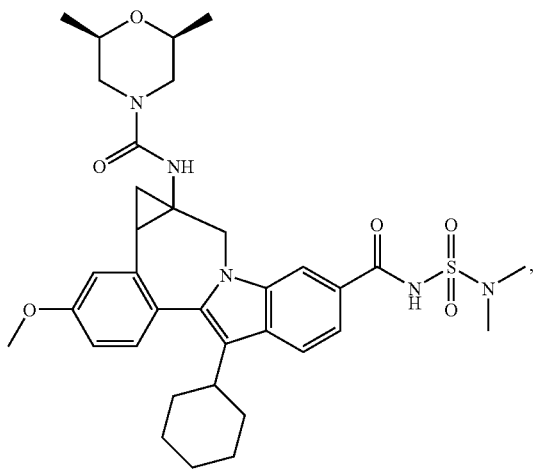

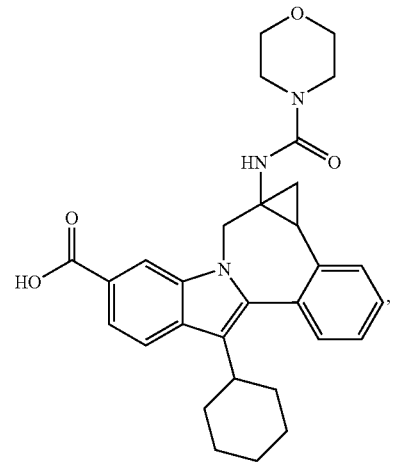

-continued
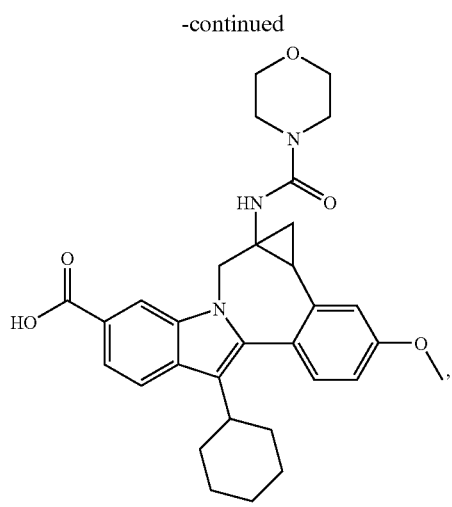
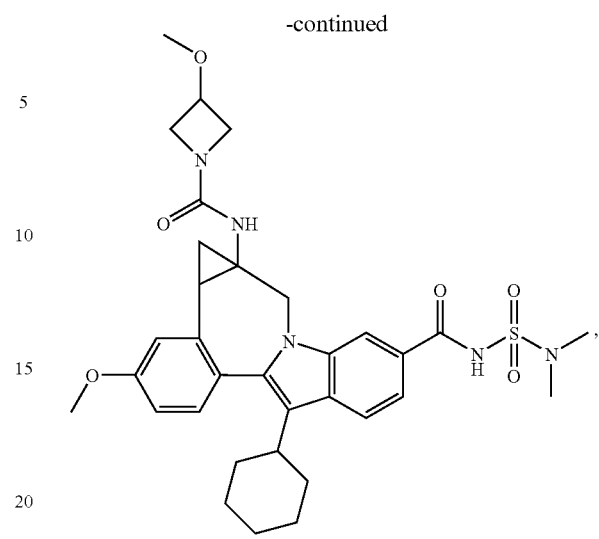
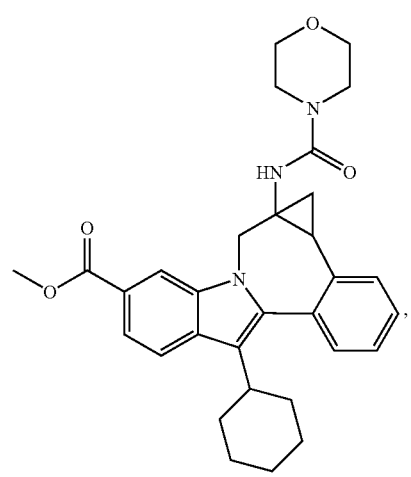
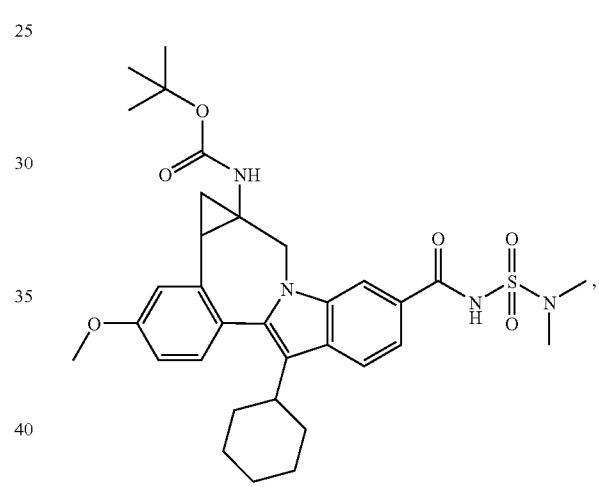
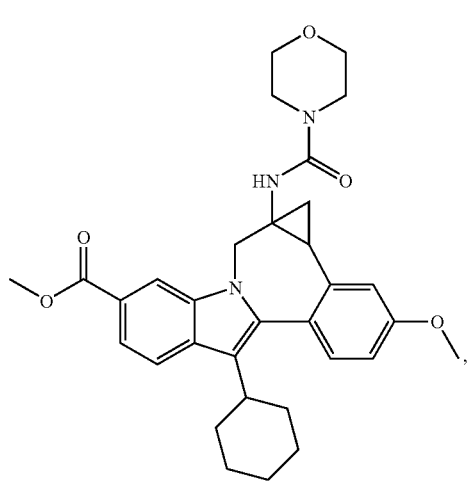
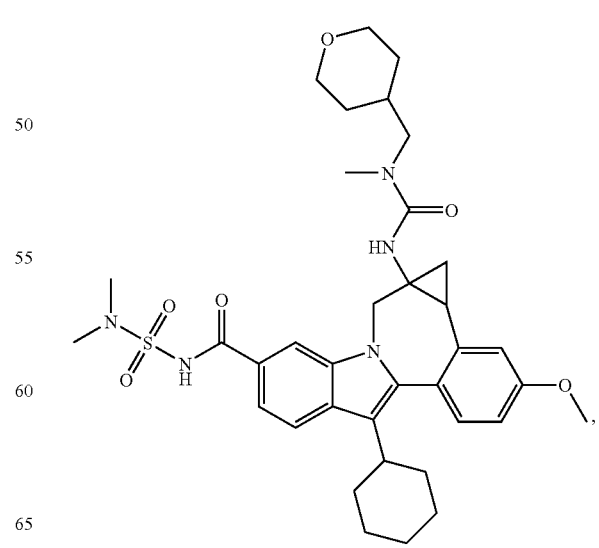

-continued
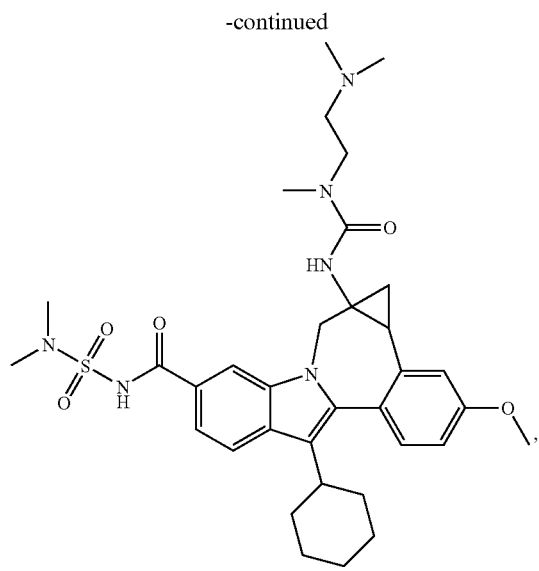
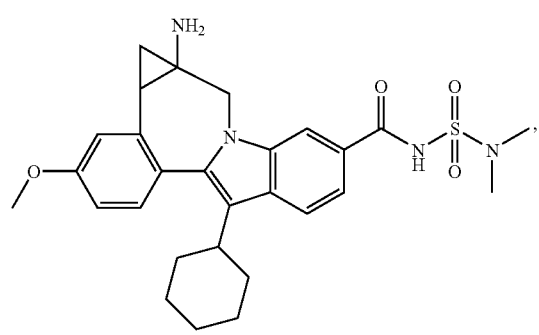
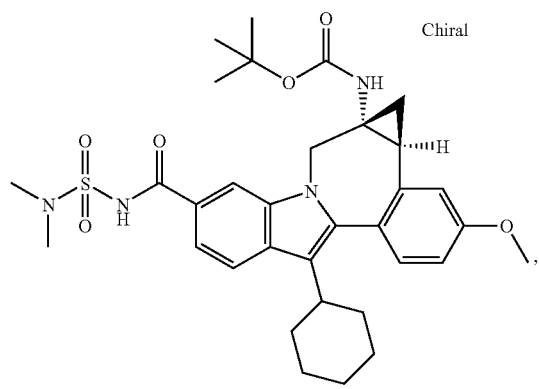
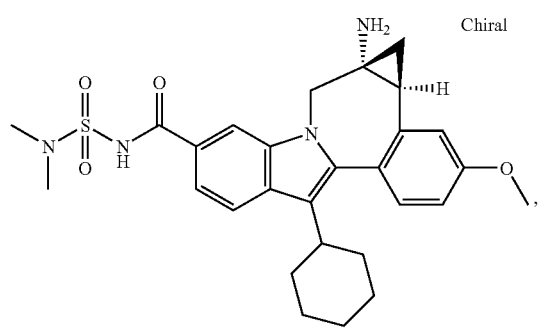
-continued
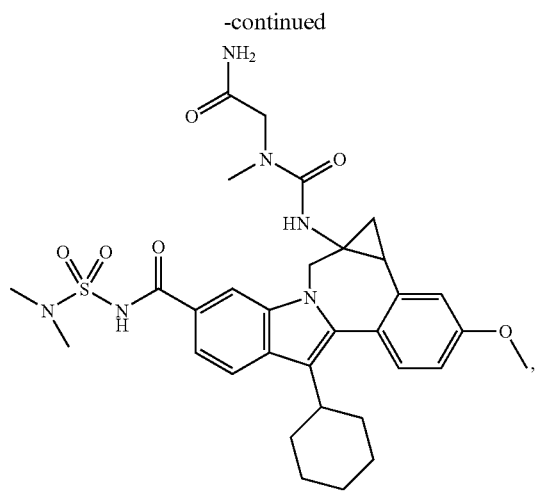
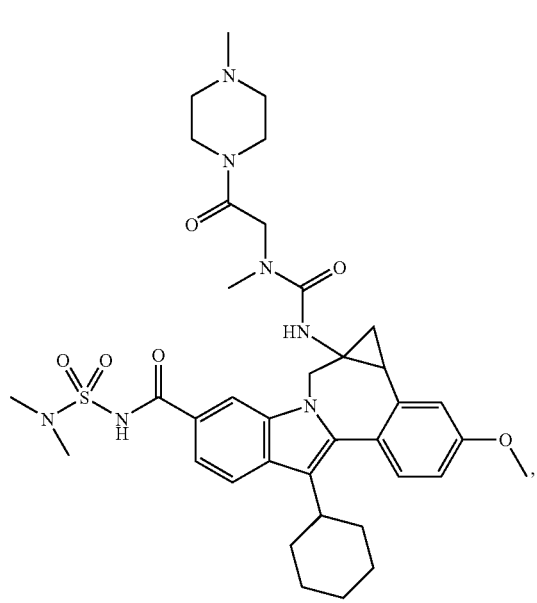
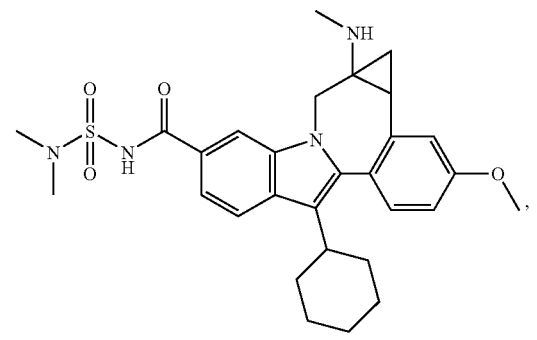

-continued

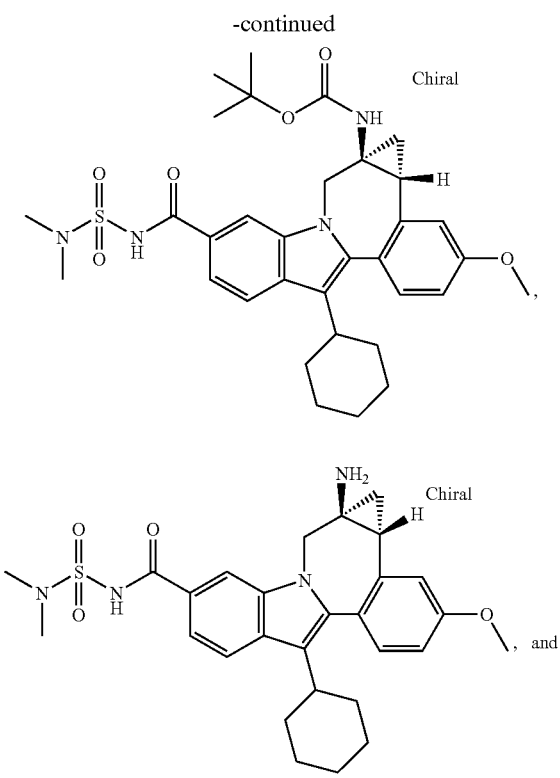

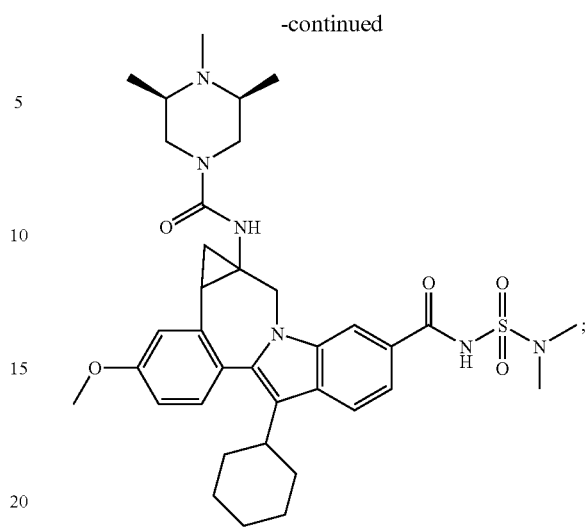

or a pharmaceutically acceptable salt thereof.

13. A composition comprising a compound of claim 1, or a pharmaceutically acceptable salt thereof, and a pharmaceutically acceptable carrier.

14. A method of treating hepatitis C infection comprising administering a therapeutically effective amount of a compound of claim 1, or a pharmaceutically acceptable salt thereof, to a patient.

* * * * *